(12) United States Patent
Tateno et al.

(10) Patent No.: US 9,500,650 B2
(45) Date of Patent: *Nov. 22, 2016

(54) UNDIFFERENTIATED CELL DETECTION METHOD AND COMPLEX CARBOHYDRATE DETECTION METHOD

(71) Applicants: National Institute of Advanced Industrial Science and Technology, Tokyo (JP); Wako Pure Chemical Industries, Ltd., Osaka (JP)

(72) Inventors: Hiroaki Tateno, Ibaraki (JP); Jun Hirabayashi, Ibaraki (JP); Yuzuru Ito, Ibaraki (JP); Yasuko Onuma, Ibaraki (JP); Makoto Asashima, Ibaraki (JP); Atsushi Kuno, Ibaraki (JP); Masaki Warashina, Hyogo (JP); Masakazu Fukuda, Hyogo (JP)

(73) Assignees: NATIONAL INSTITUTE OF ADVANCED INDUSTRIAL SCIENCE AND TECHNOLOGY, Tokyo (JP); WAKO PURE CHEMICAL INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,413

(22) PCT Filed: Oct. 31, 2012

(86) PCT No.: PCT/JP2012/006983
§ 371 (c)(1),
(2) Date: Apr. 30, 2014

(87) PCT Pub. No.: WO2013/065302
PCT Pub. Date: May 10, 2013

(65) Prior Publication Data
US 2015/0204870 A1    Jul. 23, 2015

(30) Foreign Application Priority Data

Nov. 1, 2011 (JP) ................. 2011-239919

(51) Int. Cl.
G01N 33/569 (2006.01)
C07K 14/195 (2006.01)

(52) U.S. Cl.
CPC ....... G01N 33/56966 (2013.01); C07K 14/195 (2013.01); G01N 2333/4724 (2013.01); G01N 2400/00 (2013.01)

(58) Field of Classification Search
CPC .......................... G01N 33/569; C07K 14/195
See application file for complete search history.

(56) References Cited

U.S. PATENT DOCUMENTS

2007/0020625 A1\* 1/2007 Duchaud et al. ................. 435/6
2015/0111218 A1\* 4/2015 Tateno et al. ................. 435/7.1

FOREIGN PATENT DOCUMENTS

JP       04-130274 A    5/1992
JP       09-301995 A    11/1997
(Continued)

OTHER PUBLICATIONS

Guo et al, 2004, Proc. Natl. Acad. Sci. USA 101: 9205-9210.\*
(Continued)

*Primary Examiner* — Shafiqul Haq
*Assistant Examiner* — Nam Nguyen
(74) *Attorney, Agent, or Firm* — Pearne & Gordon LLP

(57) ABSTRACT

An object of the present invention is to provide a method for evaluating a differentiation status of cells using a culture supernatant of stem cells. Provided is "undifferentiation sugar chain marker" composed of the sugar chain structure "Fucα1-2Galβ1-3GlcNAc" or "Fucα1-2Galβ1-3GalNAc" and capable of sensitively determining the undifferentiated state of stem cells using a culture supernatant of stem cells. Also found is BC2LCN lectin or a modified product thereof capable of sensitively recognizing the "undifferentiation sugar chain marker" as excellent "probe for detecting the undifferentiation sugar chain marker" capable of determining the undifferentiation status of cells using a culture supernatant.

15 Claims, 13 Drawing Sheets

(56) References Cited

FOREIGN PATENT DOCUMENTS

| | | |
|---|---|---|
| JP | 2008-187932 A | 8/2008 |
| WO | 2007/027495 A1 | 3/2007 |
| WO | 2008/087258 A1 | 7/2008 |
| WO | 2008/093828 A1 | 8/2008 |
| WO | 2009/057755 A1 | 5/2009 |

OTHER PUBLICATIONS

Tateno, et al., Glycome diagnosis of human induced pluripotent stem cells using lectin microarray, The Journal of Biological Chemistry, Jun. 10, 2011, vol. 286, No. 23, pp. 20345-20353.

Tang, et al., An antibody against SSEA-5 glycan on human pluripotent stem cells enables removal of teratoma-forming cells, Nature Biotechnology, Sep. 2011, vol. 29, No. 9, pp. 829-834 and "Online Methods" page.

Sulak, et al., A TNF-like Trimeric Lectin Domain from Burkholderia cenocepacia with Specificity for Fucosylated Human Histo-Blood Group Antigens, Structure, Jan. 13, 2010, 18 (1), pp. 59-72.

Tateno, Hiroaki, et al., Precise evaluation of iPS cells with rapid glycan profiling technique, [on-line] ASIT National Institute of Advanced Industrial Science and Technology (AIST), Jun. 22, 2011, http://www.aist.go.jp/aist_j/new_research/nr20110622/nr20110622.html (including English translation).

Suemori, et al., Efficient establishment of human embryonic stem cell lines and long-term maintenance with stable karyotype by enzymatic bulk passage, Biochemical and Biophysical Research Communications, 2006, 345, pp. 926-932.

Draper et al., Surface antigens of human embryonic stem cells: changes upon differentiation in culture, J. Anat. 2002, 200, pp. 246-258.

Iijima, et al., Position-Specific Incorporation of Fluorescent Non-natural Amino Acids into Maltose-Binding Protein for Detection of Ligand Binding by FRET and Flourescence Quenching, ChemBioChem, 2009, 10, pp. 999-1006.

Tateno, et al., Frontal Affinity chromatography: sugar-protein interactions, Nature Protocols, 2007, vol. 2, No. 10, pp. 2529-2537.

Nielsen, et al., The Role of Podocalyxin in Health and Disease, J. Am. Soc. Nephrol, 2009, 20, pp. 1669-1676.

International Search Report issued in PCT/JP2012/006983, Jan. 22, 2013.

The partial supplementary European Search Report issued in corresponding European Patent Application No. 12845274.5, Mailing Date: Apr. 15, 2015.

Cooper, et al., "Biochemical properties of a keratan sulphate/chondroitin sulphate proteoglycan expressed in primate pluripotent stems cells," Journal of Anatomy, 2002, vol. 200, pp. 259-265, Anatomical Society of Great Britain and Ireland 2002.

* cited by examiner glycan a $Ka = 2.5.E+04$

UNDIFFERENTIATED CELL DETECTION METHOD AND COMPLEX CARBOHYDRATE DETECTION METHOD

TECHNICAL FIELD

The present invention relates to a method for determining the state of cells using a cell culture supernatant. Particularly, it relates to a method for evaluating the presence or absence of undifferentiated cells. The present invention also relates to a method for detecting a substance to be detected having a sugar chain, such as a glycoprotein.

BACKGROUND ART

Pluripotent stem cells have attracted attention because of having the property of being capable of differentiating into various cells constituting the body and the property of being capable of maintaining their characteristics being undifferentiated, and are not only applied to drug discovery screening and elucidation of disease mechanisms but also under world-wide study as a material for regenerative medicine.

The world's first phase 1 clinical trial using human ES cells started against acute spinal-cord injury in the U.S.A in 2010; furthermore, an investigational new drug (IND) application for phase ½clinical trials using human ES cells against retinal degenerative disease was approved by FDA; and regenerative medicine research using human pluripotent stem cells continues rapid development.

Particularly, iPS cells as new human pluripotent stem cells originating in Japan have great advantage that they have a low ethical roadblock because of, for example, no use of fertilized embryos and can be established also from autologous tissue, and thus they are receiving high expectations from the field of regenerative medicine. In Japan, Riken Center for Developmental Biology, Institute of Biomedical Research and Innovation Laboratory, and other institutes plan to start clinical studies using iPS cells with age-related macular degeneration patients in fiscal 2013, and Keio University also intends to start clinical studies in spinal cord injury patients in 2015.

As the clinical application of human pluripotent stem cells such as ES cells and iPS cells are started as just described above, a system to supply cells by securing quality and safety is not sufficiently developed. For pluripotent stem cells, the preparation method, culture conditions, storage conditions, and the like affect qualities such as characteristics being undifferentiated, differentiation potency, and proliferative capacity. Thus, managements not based on an appropriate method may produce results different for each producer and each user. This becomes a cause of bringing negative effects such as the decreased reliability of stem cell therapy and the occurrence of health hazards due to the therapy. Thus, there are necessary a maintenance culture method high in reliability and reproducibility and a measurement/evaluation system.

For example, although pluripotent stem cells are not directly used but used after differentiating them into desired cells for transplantation in a cell therapy, it has been pointed out that if a cell source having differentiated into desired cells is contaminated with undifferentiated cells, these undifferentiated cells become a cause of tumorgenesis. Accordingly, there is a need for the development of a technique for evaluating whether cells to be used for cell therapy are contaminated with undifferentiated cells, i.e., tumorgenic cells.

In contrast, somatic stem cells, which are various compared to human pluripotent stem cells including ES cells and iPS cells, have been in clinical application as established techniques. However, it is not easy to stably obtain cells having quality suitable for transplantation; thus, it represents a very important challenge to establish a quality verification method for mesenchymal stem cells and a stable culture method based thereon. There is also a need for the development of a quality verification method for cells before transplantation in evaluating the effectiveness of cell transplantation using somatic stem cells, understanding the mechanism thereof, and evaluating risk.

Previously, the present inventors exhaustively analyzed the sugar chain profiles of human iPS cells (114 specimen) prepared from 5 types of different somatic cells (skin, fetal lung, endometrial membrane, placental artery, and amniotic membrane) and human ES cells (9 specimen), using lectin microarray.

As a result, despite the different sugar chain profiles of the original somatic cells for each tissue, it was found that all of the prepared iPS cells showed almost the same sugar chain profile and the introduction of reprograming genes caused uniform convergence into sugar chain structures analogous to those of ES cells. According to the results of analyzing the lectin array data of human ES/iPS cells and human somatic cells in detail, the expression level of α2-6Sia, α1-2Fuc, and type 1 LacNAc was presumed to be markedly increased in undifferentiated human ES/iPS cells compared to in somatic cells. In addition, rBC2LCN was found to bind only to undifferentiated human ES/iPS cells by expression analysis of glycosyltransferase genes using DNA array and a method using a mass spectrometer (Non Patent Literature 1).

The rBC2LCN described above is a recombinant BC2LCN lectin (YP_002232818) that corresponds to the N-terminal domain of the BC2L-C protein derived from a gram-negative bacterium (Burkholderia cenocepacia), and is expressed in transformed Escherichia coli, and is a lectin recognizing the sugar chain structures "Fucα1-2Galβ1-3GlcNAc" and "Fucα1-2Galβ1-3GalNAc" in the nonreducing terminus of a complex sugar chain (Non Patent Literatures 1 and 3).

In the above-described experiment using the lectin array, the present inventors found that rBC2LCN reacted with undifferentiated human ES/iPS cells but completely failed to react with differentiated somatic cells (skin, fetal lung, endometrial membrane, placental artery, and amniotic membrane). It is construed that rBC2LCN specifically reacts with the sugar chain structures "Fucα1-2Galβ1-3GlcNAc (=H type 1 structure)" and "Fucα1-2Galβ1-3GalNAc (=H type 3 structure)" having 2 (α1-2Fuc and typel LacNAc) of "α1-2Fuc", "typel LacNAc", and "α2-6Sia". These two sugar chain structures are sugar chains highly expressed on human ES/iPS cells and hardly expressed on differentiated cells of the skin, fetal lung, endometrial membrane, placental artery, and amniotic membrane.

This indicates that the sugar chain ligand recognized by rBC2LCN is a novel undifferentiation sugar chain marker characterizing undifferentiated cells and also indicates that rBC2LCN can be used as a probe specific for the undifferentiation sugar chain markers "Fucα1-2Galβ1-3 GlcNAc" and/or "Fucα1-2Galβ1-3GalNAc" (hereinafter, both are sometimes together referred to as "Fucα1-2Galβ1-3GlcNAc/GalNAc").

Thereafter, the team of Drukker et al. also found that an antibody recognizing "Fucα1-2Galβ1-3GlcNAc" recognizes ES and iPS cells in an undifferentiated state (Non Patent Literature 2), supporting the above findings of the present inventors.

However, the antibody of Drukker et al. specifically reacts with "Fucα1-2Galβ1-3GlcNAc (=H type 1 structure)" but does not react with "Fucα1-2Galβ1-3GalNAc (=H type 3 structure)". When the antibody is compared with rBC2LCN, it cannot detect "Fucα1-2Galβ1-3GalNAc" or "sugar chains containing Fucα1-2Galβ1-3GalNAc" in undifferentiated cells; thus, the antibody has a disadvantage of having sensitivity not sufficiently increased when compared with rBC2LCN of the present inventors.

CITATION LIST

Patent Literature

Patent Literature 1
 Japanese Patent Laid-Open No. 09-301995
Patent Literature 2
 WO 2007/027495

Non Patent Literature

Non Patent Literature 1
 Tateno H, Toyota M, Saito S, Onuma Y, Ito Y, Hiemori K, Fukumura M, Matsushima A, Nakanishi M, Ohnuma K, Akutsu H, Umezawa A, Horimoto K, Hirabayashi J, Asashima M., J. Biol. Chem. 2011, 286(23): 20345-53.
Non Patent Literature 2
 Tang C, Lee AS, Volkmer JP, Sahoo D, Nag D, Mosley AR, Inlay MA, Ardehali R, Chavez SL, Pera RR, Behr B, Wu JC, Weissman IL, Drukker M., Nat. Biotechnol. 2011, 29(9): 829-34.
Non Patent Literature 3
 Sulak O, Cioci G, Delia M, Lahmann M, Varrot A, Imberty A, Wimmerova M., Structure. 2010, 18(1): 59-72.
Non Patent Literature 4
 Suemori H., Yasuchika K., Hasegawa K., Fujioka T., Tsuneyoshi N., Nakatsuji N. Biochem. Biophys. Res. Commun. 2006, 345, 926-932.
Non Patent Literature 5
 Draper J S, Pigott C, Thomson J A, Andrews P W, J. Anat. 2000, 200, 249-58.
Non Patent Literature 6
 Iijima et al., Chem. Bio. Chem. 2009, 10, 999-1006.
Non Patent Literature 7
 Tateno, H., Nakamura-Tsuruta, S., and Hirabayashi, J. Nat. Protoc. 2007, 2, 2529-2537.
Non Patent Literature 8
 Nielsen, J. S., and McNagny, K. M. J. Am. Soc. Nephrol., 2009, 20, 1669-1676.

SUMMARY OF INVENTION

Technical Problem

Currently, when the quality of cells is inspected, it is common to analyze the difference in the gene expression of cells, the epigenomic state, the cell surface marker, or the like using a means such as a sequencer, microarray, flow cytometry, or immunohistochemistry. However, these methods require the use of cells themselves for analysis; thus, the methods have a big problem that they not only require a cumbersome step of recovering cells but also use valuable cells for use in cell therapy, in the inspection.

As described above, the present inventors have identified sugar chain structures themselves providing undifferentiation sugar chain markers that distinguishing between undifferentiated cells and differentiated cells. However, the previous technique of the present inventors using rBC2LCN as well as the method of Drukker et al. are little more than conventional techniques in that sugar chains of cell surface glycoproteins, glycolipids, or the like are observed. In other words, these techniques are similar in terms of requiring a step of recovering test cells or a further step of purification, and have not resolved the conventional problems of the cumbersomeness of the step during detection and evaluation and the waste of useful cells.

Accordingly, the main object of the present invention is to provide a method for noninvasively inspecting the state of cells without decreasing test cells.

Solution to Problem

The present inventors have prepared a substrate in which rBC2LCN as a probe specific for "Fucα1-2Galβ1-3GlcNAc/GalNAc" is immobilized on a glass slide, and in evaluating the differentiated state of ES cells and iPS stem cells using the substrate, simultaneously attempted to assess reactivity with a culture supernatant in place of cells themselves (a crushed product thereof).

As a result, it has been surprisingly found that rBC2LCN on the substrate enables the evaluation of the differentiation status by simply supplying a drop (corresponding to 1 μL) of the culture supernatant collected from the test cell medium directly in a state not subjected to any purification step onto the lectin on the substrate surface. Specifically, rBC2LCN has not reacted with a control medium or a culture supernatant of iPS cells differentiated by culture in the presence of retinoic acid, whereas it has specifically reacted with a culture supernatant of iPS cells maintaining the undifferentiated state in the absence of retinoic acid.

The above results indicate that the undifferentiation sugar chain marker having the sugar chain structure "Fucα1-2Galβ1-3GlcNAc/GalNAc" is always secreted into the culture supernatant of undifferentiated cells but decreases as differentiation proceeds by the induction of differentiation and the undifferentiation sugar chain marker disappears on complete differentiation.

This corresponds to the fact that not only the invention of the present application has first found the functioning of the "Fucα1-2Galβ1-3GlcNAc/GalNAc" sugar chain as an undifferentiation sugar chain marker observable in a culture supernatant but also the present invention has first provided the undifferentiation sugar chain marker observable in a culture supernatant. To the present inventors' knowledge, no findings have previously existed showing that the glycoprotein, glycolipid, or the like of the cell surface of ES cells and iPS stem cells maintained in an undifferentiated state under culture can be secreted in a detectable state into the culture medium.

In other words, it has been shown that when the differentiated state is evaluated during the differentiation of undifferentiated cells such as ES cells and iPS cells, or to evaluate the state during culture of these undifferentiated cells while maintaining the undifferentiated state, a culture supernatant of these undifferentiated cells can be collected to evaluate the presence/absence of "Fucα1-2Galβ1-3GlcNAc/GalNAc" in the culture supernatant using a lectin, an antibody, or the like specific for the sugar chain structure. The method using a culture supernatant can be said to be a very simple technique not requiring the step of recovering test cells of interest or the step of purifying a particular molecule of interest. Particularly, "BC2LCN lectin" has the property of sensitively recognizing both of the sugar chain structures of "Fucα1-2Galβ1-3GlcNAc" and "Fucα1-2Galβ1-3GalNAc"; thus, the lectin can be used to provide a more reliable system for evaluating the undifferentiated state.

The present invention has been accomplished by obtaining the above findings.

Thus, the present invention encompasses the following inventions.

[1] A method for determining a differentiation status of a stem cell, comprising measuring the presence or absence or an amount of an undifferentiation sugar chain marker represented by formula 1:

[Formula 1]

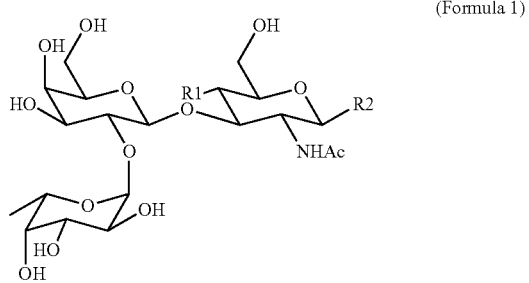

(Formula 1)

wherein R1 represents an OH group or any sugar chain and R2 represents an OH group or any sugar chain, protein, lipid, or another molecule, or formula 2:

[Formula 2]

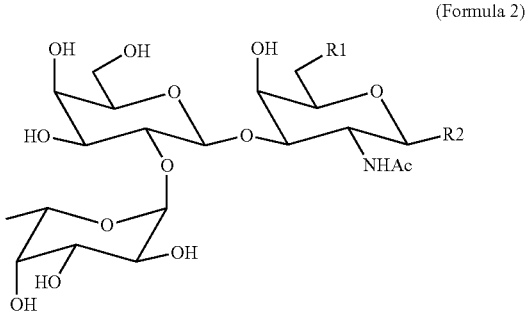

(Formula 2)

wherein R1 represents an OH group or any sugar chain and R2 represents an OH group or any sugar chain, protein, lipid, or another molecule, in a culture supernatant of stem cells.

According to the method, the differentiation status of cells can be evaluated using a supernatant of a culture in which cells are cultured, rather than cells themselves.

[2] The method according to [1] above, wherein the presence or absence or the amount of the undifferentiation sugar chain marker is measured using a protein specifically recognizing the sugar chain structure represented by formula 1 or 2.

[3] The method according to [2] above, wherein the protein is a protein as described below:

a protein comprising the amino acid sequence set forth in SEQ ID NO: 1 or an amino acid sequence in which one or several amino acids are deleted, substituted, inserted, or added in the shown amino acid sequence, and specifically recognizing the sugar chain structure represented by formula 1 or 2 above.

[4] The method according to any one of [1] to [3] above, wherein the culture supernatant of the stem cell is a culture supernatant after the stem cell is subjected to a differentiation induction treatment.

[5] The method according to any one of [1] to [4] above, comprising measuring the presence or absence or the amount of the undifferentiation sugar chain marker represented by formula 1 and/or 2 above derived from podocalyxin.

[6] The method according to [1] to [5] above, comprising detecting the undifferentiation sugar chain marker by a lectin-lectin sandwich method using a protein specifically recognizing the sugar chain structure represented by formula 1 or 2 above, comprising the amino acid sequence set forth in SEQ ID NO: 1 or an amino acid sequence in which one or several amino acids are deleted, substituted, inserted, or added in the shown amino acid sequence, and having no sugar chain.

[7] A method for obtaining a differentiated cell being not contaminated with an undifferentiated cell, comprising collecting after confirming the absence of an undifferentiation sugar chain marker represented by formula 1:

[Formula 3]

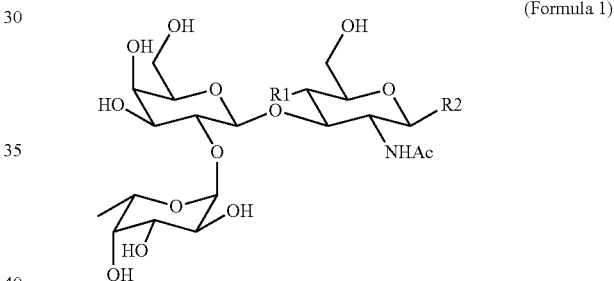

(Formula 1)

wherein R1 represents an OH group or any sugar chain and R2 represents an OH group or any sugar chain, protein, lipid, or another molecule, or formula 2:

[Formula 4]

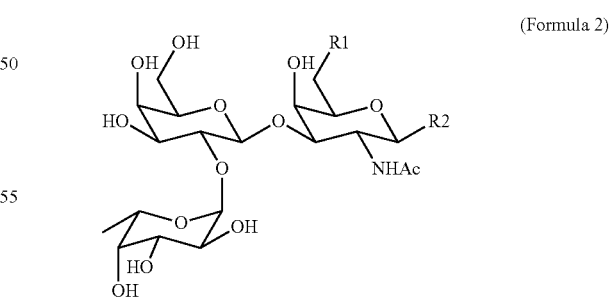

(Formula 2)

wherein R1 represents an OH group or any sugar chain and R2 represents an OH group or any sugar chain, protein, lipid, or another molecule, in a culture supernatant of the stem cell subjected to a differentiation induction treatment.

[8] The method according to [7] above, wherein the confirmation of the absence of the undifferentiation sugar chain marker is made using a protein comprising the amino acid sequence set forth in SEQ ID NO: 1 or an amino acid sequence in which one or several amino acids are deleted, substituted, inserted, or added in the shown amino acid sequence and specifically recognizing a sugar structure represented by formula 1 or 2 above.

[9] A kit for use in a method for determining a differentiation status of a stem cell, comprising a protein specifically recognizing a sugar chain structure represented by formula 1:

[Formula 5]

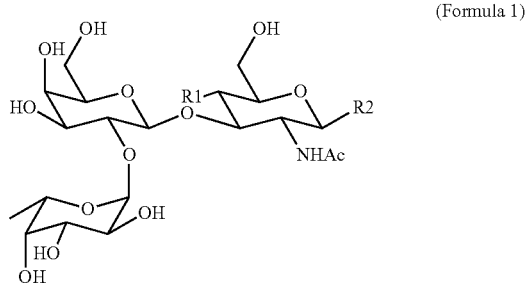

(Formula 1)

wherein R1 represents an OH group or any sugar chain and R2 represents an OH group or any sugar chain, protein, lipid, or another molecule, or formula 2:

[Formula 6]

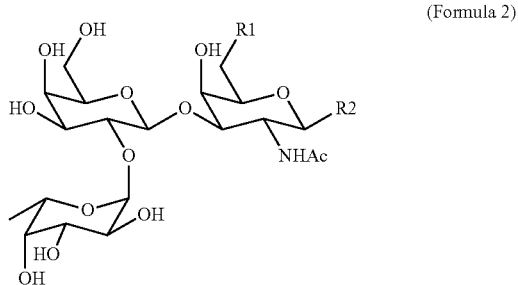

(Formula 2)

wherein R1 represents an OH group or any sugar chain and R2 represents an OH group or any sugar chain, protein, lipid, or another molecule.

[10] The kit according to [9] above, wherein the protein is a protein as described below: a protein comprising the amino acid sequence set forth in SEQ ID NO: 1 or an amino acid sequence in which one or several amino acids are deleted, substituted, inserted, or added in the shown amino acid sequence and specifically recognizing a sugar chain structure represented by formula 1 or 2 above.

Advantageous Effects of Invention

According to the method for determining a differentiation status of a stem cell in accordance with the present invention, the status of cells can be noninvasively evaluated without destroying the cells by directly reacting a culture supernatant of test cells with a protein specific for an undifferentiation sugar chain marker, such as a lectin. Thus, the present invention can be expected to be applied to regenerative medicine, biologics, and the like because it can be used particularly for simply and efficiently determining the state of undifferentiated cells.

DESCRIPTION OF EMBODIMENTS

Figure 1:
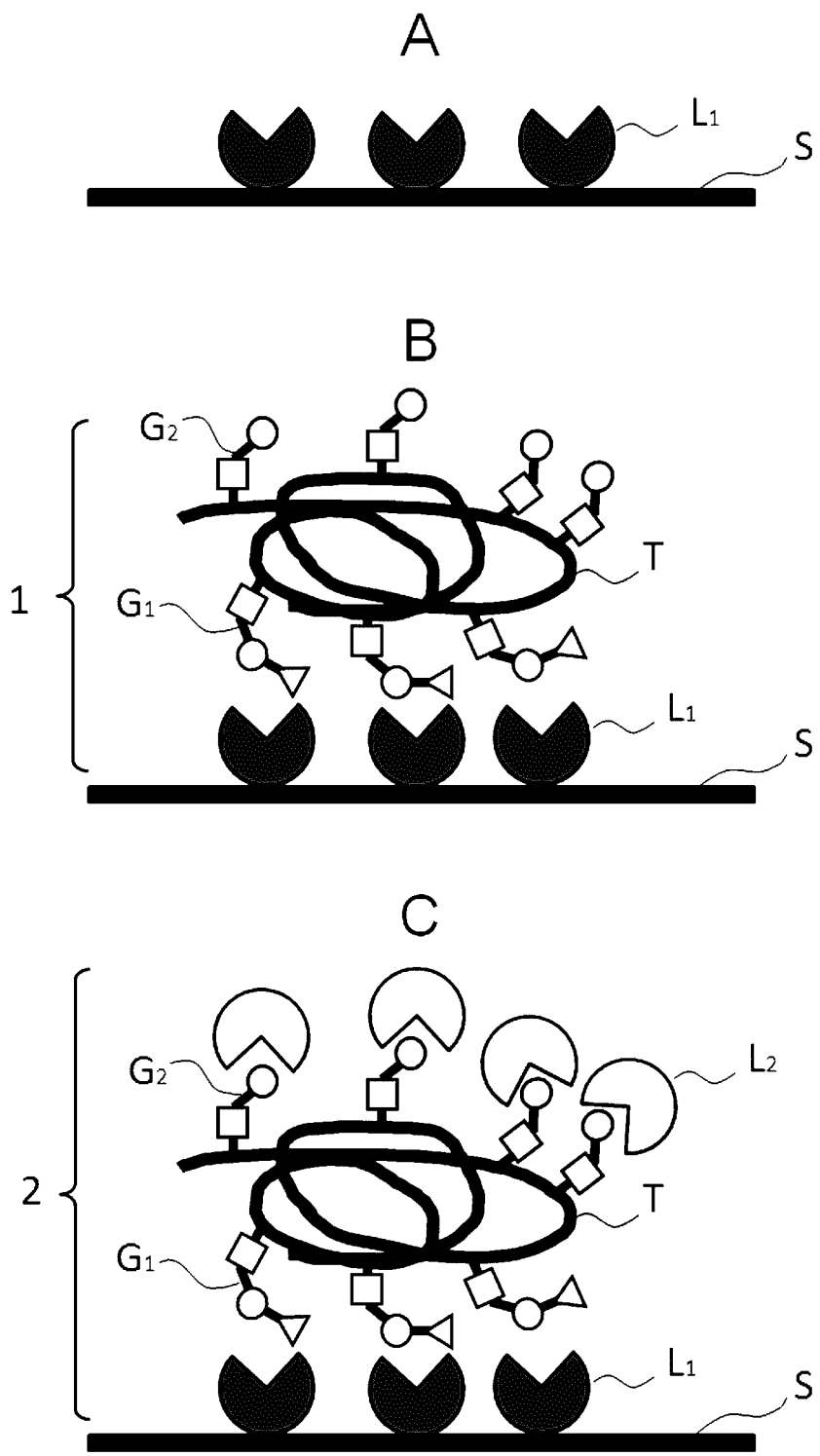
FIG. 1 is a diagram for explaining an example of concrete steps of a lectin-lectin sandwich method.

A. Method Etc. for Determining Differentiated State of Stem Cell

1. Undifferentiation Sugar Chain Marker Measurable in Culture Supernatant According to Present Invention The undifferentiation sugar chain marker measurable in a culture supernatant according to the present invention (hereinafter also simply referred to as "undifferentiation sugar chain marker") is a complex carbohydrate, such as a glycoprotein or a glycolipid, which has the sugar chain structure "Fucα1-2Galβ1-3GlcNAc/GalNAc", i.e., "Fucα1-2Galβ1-

3GlcNAc (H type 1 sugar chain)" or "Fucα1-2Galβ1-3Gal-NAc (H type 3 sugar chain)" and is prominently expressed on the cell surface of human ES/iPS cells. In Example 8 to be described later, podocalyxin was identified as a complex carbohydrate. The structure of the sugar chain of podocalyxin was expected to contain "Fucα1-2Galβ1-3GalNAc (=H type 3 sugar chain)".

The present invention is an invention characterized by having first found that these two sugar chains are always secreted into a culture supernatant for cells in an undifferentiated state, such as ES cells and iPS cells, while the secretion into a culture supernatant is absent for differentiated somatic cells, that is, these sugar chain ligands are secreted into the supernatant of cells only in the case of the undifferentiated state; and these sugar chain ligands are useful as "undifferentiation sugar chain markers measurable in a supernatant of cells".

For the sugar chain structure "Fucα1-2Galβ1-3GlcNAc", the hydroxyl group of position 4 of GlcNAc may be substituted by a monosaccharide (preferably fucose) or a branched or non-branched oligosaccharide chain (preferably a sugar chain consisting of 2 to 5 saccharides). The sugar chain structure is a sugar chain binding to the nonreducing terminus of a glycoprotein, a glycolipid, a saccharide, or the like at position 1 of GlcNAc as a membrane constituent on the surface of undifferentiated stem cells; thus, it also binds to the nonreducing terminus of a OH group or another saccharide, protein or lipid, or a different molecule at position 1 of GlcNAc, as a sugar chain structure secreted into the culture supernatant of stem cells in an undifferentiated state. Thus, the sugar chain structure can be represented as formula 1:

[Formula 7]

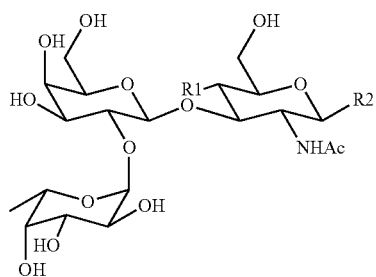

(Formula 1)

wherein R1 represents an OH group or any sugar chain, such as a 4αFuc group and R2 represents an OH group or any sugar chain, protein, lipid, or another molecule.

Similarly, for the sugar chain structure "Fucα1-2Galβ1-3GalNAc", the hydroxyl group of position 1 of GalNAc may be substituted by a branched or non-branched oligosaccharide chain (preferably a sugar chain consisting of 2 to 5 saccharides). The sugar chain structure is a sugar chain binding to the nonreducing terminus of a glycoprotein, a glycolipid, a saccharide, or the like at position 1 of GalNAc as a membrane constituent on the surface of undifferentiated stem cells; thus, it also binds to the nonreducing terminus of an OH group or another saccharide, protein or lipid, or a different molecule at position 1 of GalNAc, as a sugar chain structure secreted into the culture supernatant of stem cells in an undifferentiated state. Thus, the sugar chain structure can be represented as formula 2:

[Formula 8]

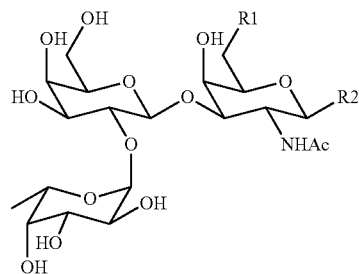

(Formula 2)

wherein R1 represents an OH group or any sugar chain such as a Galβ1-4Glc group and R2 represents an OH group or any sugar chain, protein, lipid, or another molecule.

2. Probe for Detecting "Undifferentiation Sugar Chain Marker" According to Present Invention The probe for detecting the undifferentiation sugar chain marker "Fucα1-2Galβ1-3GlcNAc (formula 1)" or "Fucα1-2Galβ1-3GalNAc (formula 2)" in a culture supernatant according to the present invention may be generally a protein probe, and may be any probe provided that it is a protein specifically binding to the undifferentiation sugar chain marker. Typically, BC2LCN or a modified product thereof is preferably used which is a lectin recognizing both sugar chain structures of formulas 1 and 2 above found by the present inventors; however, a lectin recognizing formula 1 or 2 may be used.

In addition to such lectins, other proteins may be used, such as an antibody or a fragment thereof or TCR or a fragment thereof capable of recognizing the undifferentiation sugar chain marker. Specific examples thereof can include the "Fucα1-2Galβ1-3GlcNAc (=H type 1 sugar chain)" antibody of Drukker et al. (Non Patent Literature 2).

As will be described later, a kit for determining the differentiation status of stem cells can be made by using a substrate on which the probe for detecting "undifferentiation sugar chain marker" according to the present invention is immobilized as well as a means for contacting the substrate surface with a culture supernatant of stem cells and a means for labeling the detection probe immobilized on the substrate or the culture supernatant, as a set. Particularly, the use of BC2LCN or a modified product as a probe for detecting "undifferentiation sugar chain marker" can provide a kit capable of highly sensitively determining the differentiation status of stem cells.

As used herein, "substrate" is not limited to a flat-shaped material such as a glass slide and includes bases of any shape and material to which conventional protein immobilization methods can be applied, such as an ELISA plate, a magnetic bead, and a filter. "Substrate material" is preferably a substance used in conventional microarray, and there are used a silicon wafer, glass, polycarbonate, a membrane, a polymer film such as polystyrene or polyurethane, and a porous substance.

3. rBC2LCN

As described in 2. above, according to the present invention, as a probe for detecting the undifferentiated sugar chain (H type 1 sugar chain and/or H type 3 sugar chain), i.e., the sugar chain structure of formula 1 or 2, any protein exhibiting binding specificity to these sugar chain structures can be used; however, the most preferable lectin among these is "rBC2LCN" previously found by the present inventors. Thus, "rBC2LCN" will be described below.

For the purpose of the present invention, "rBC2LCN" refers to a recombinant of a lectin found in a gram-negative bacterium (*Burkholderia cenocepacia*) expressed in *Escherichia coli*; this lectin corresponds to the N-terminal domain of a protein called BC2L-C (GenBank/NCBI-GI Accession No. YP_002232818) (Non Patent Literature 3). rBC2LCN is known to show structural similarity to TNF-like protein and form a trimer. Analysis using a sugar chain array has demonstrated that the lectin exhibits binding specificity to "Lewis b sugar chain (Fucα1-2Galβ1-3 (Fucα1-4)GlcNAc)" or "Globo H sugar chain (Fucα1-2Galβ1-3GalNAcβ1-3Galα1-4Galβ1-4Glc)" as a sugar chain structure containing "Fucα1-2Galβ1-3GlcNAc (H type 1 sugar chain)" or "Fucα1-2Galβ1-3GalNAc (H type 3 sugar chain)", as well as H type 1 and H type 3 sugar chains.

rBC2LCN can be bulk-produced even by transformed bacteria because it contains no sugar chain. Specifically, BC2LCN gene encoding the amino acid sequence of GenBank/NCBI-GI Accession No. YP_002232818 (SEQ ID NO: 1) (Genome ID: 206562055) can be used, expressed in transformed *Escherichia coli* after properly optimizing it for the host, and purified by a conventional protein purification means.

In this regard, BC2LCN does not require the whole length corresponding to SEQ ID NO:1, and even if it is a sequence in which some amino acids are partially deleted, substituted, inserted, or added in SEQ ID NO: 1, it will do if it maintains the property of specifically recognizing "Fucα1-2Galβ1-3GlcNAc/GalNAc", i.e., a sugar chain structure represented by formula 1 or 2.

Specifically, BC2LCN or a modified product thereof of the present invention can be expressed, for example, as follows.

"A protein comprising the amino acid sequence set forth in SEQ ID NO: 1 or an amino acid sequence in which one or several amino acids are deleted, substituted, inserted, or added in the shown amino acid sequence and specifically recognizing the sugar chain structure "Fucα1-2Galβ1-3GlcNAc" or "Fucα1-2Galβ1-3GalNAc".

If the sugar chain structure is expressed using the formula 1 or 2, it can be expressed as "a protein comprising the amino acid sequence set forth in SEQ ID NO: 1 or an amino acid sequence in which one or several amino acids are deleted, substituted, inserted, or added in the shown amino acid sequence and specifically recognizing a sugar chain structure represented by the formula 1 or 2".

Here, the "several" represents a natural number of 20 or less, preferably 10 or less, more preferably 5 or less.

4. Detection and Measurement of "Undifferentiation Sugar Chain Marker" of Present Invention (1) Method for Collecting Culture Supernatant According to the present invention, a given amount of a culture supernatant of undifferentiated stem cells or cells after differentiation induction is collected using a micropipette or the like and analyzed for reactivity to a protein specifically binding to the undifferentiation sugar chain marker of the present invention. The culture medium is generally replaced with a fresh culture medium every certain period of time (about 1 day). Thus, the detection of the undifferentiation sugar chain marker is performed after a detectable amount of the undifferentiation sugar chain marker is secreted into the culture medium after replacement, from undifferentiated cells or insufficiently differentiated cells. After the culture medium is replaced, the time required for the elution of a detectable amount of the undifferentiation sugar chain marker into the culture medium can vary depending on the type of cells and the culture conditions. Thus, after the culture medium is replaced, the time until the collection of the culture supernatant used for the detection of the undifferentiation sugar chain marker can be properly set depending on the type of cells and the culture conditions; however, for example, it is considered to be on the order of 18 to 30 hours. The medium is typically replaced every 24 hours or so; thus, it is preferable to use the culture supernatant discarded at the time.

According to such an analysis method, cells in a well, dish, or flask can be evaluated as a cell group consisting of only differentiated cells that have not any longer contaminated with undifferentiated cells, if the undifferentiation sugar chain marker is no longer detected (have decreased to the same level as the background value) in the supernatant from the well, dish, or flask upon induction of differentiation of stem cells in an undifferentiated state; thus, differentiated cells having no risk of contamination of undifferentiated cells can be rapidly obtained in large quantity in a well-, dish- or flask-scale.

Here, the method for "differentiation induction" of stem cells into neuronal cells, digestive system cells, or the like may be any method; for example, various known methods can be applied, including a method for culturing stem cells in the presence of retinoic acid to differentiate them into neuronal cells and a method for forming epidermal cells on the surface of NIH3T3 cells whose growth have been stopped. Because the expression level of the undifferentiation sugar chain marker of the present invention on the surface of differentiated cells is of a negligible extent, noise is expected to be extremely reduced under any induction differentiation conditions.

For the quality control of stem cells whose undifferentiated state is desired to be maintained, the amount of the undifferentiation sugar chain marker of the present invention is measured by collecting a culture supernatant periodically or as needed or using the culture supernatant discarded in replacing the medium, which enables it to be confirmed whether all cells during storage are maintained in the undifferentiated state. For example, typical methods for culturing stem cells while maintaining the undifferentiated state thereof include a method which involves culturing them on the surface of feeder cells such as mouse fibroblasts; however, in the method, the culture supernatant is withdrawn and replaced with fresh medium at least once a day. The culture supernatant withdrawn and discarded can be used to determine differentiation/undifferentiation.

Here, the means for collecting a given amount of the culture supernatant may be handwork but is reliably automatic and mechanical collection using an automatic culture apparatus; particularly, in an attempt to obtain only a group of differentiated cells that have not contaminated with undifferentiated cells as soon as possible after differentiation induction, only a group of differentiated cells can be reliably and rapidly obtained by collection every a certain period of time for analysis.

(2) Method for Analyzing "Undifferentiation Sugar Chain Marker" of Present Invention A lectin, an antibody, or the like as a protein capable of specifically binding to the undifferentiation sugar chain marker of the present invention can be labeled and directly added to a culture supernatant to measure the intensity of labeling; however, preferably, the lectin, the antibody, or the like is immobilized on a substrate, and the culture supernatant is fluorescently labeled with "Cy3-NHS ester" (from GE Healthcare Bioscience Corporation) or the like to perform detection and measurement by an ELISA method, a method using an evanescent wave excitation fluorescence scanner, or the like.

The culture supernatant collected from the culture medium of stem cells is provided for a detection step directly without passing through a purification step, or after dilution, or after concentrating it using the antibody, the lectin, or the like in advance. Detection can be performed using a confocal scanner, a fluorescence plate reader, or the like in addition to a method involving contacting with the surface of a lectin immobilized on the substrate previously developed by the present inventors and using an evanescent wave excitation fluorescence scanner. The same method can also be applied to the immobilized antibody.

However, the measurement of binding activity is not limited to the above method and can also be performed by a method such as ELISA, a surface plasmon resonance sensor, an equilibrium dialysis method, titration calorimetry, or a crystal oscillator sensor detection method. The undifferentiation sugar chain marker according to the present invention can also be measured by a conventional competition method or "lectin-lectin sandwich method" to be described later. The use of "lectin-lectin sandwich method" enables the measurement of the undifferentiation sugar chain marker in the culture supernatant with a good quantitativity; thus, the completion of differentiation (disappearance of undifferentiated cells) can be determined with better accuracy.

The culture supernatant after differentiation induction can be subjected to the above analysis to confirm no contamination with undifferentiated cells, followed by separating and collecting cells in the well, dish, or flask to provide differentiated cells. In contrast, for a method for culturing stem cells in a state kept in a state remaining undifferentiated, the above analysis method can be applied to the culture supernatant to be discarded in replacing the medium to confirm the quality-keeping state of stem cells.

(3) Kit or Apparatus for Determining Differentiation Status of Stem Cell by Analyzing "Undifferentiation Sugar Chain Marker" of Present Invention If a probe for detecting the undifferentiation sugar chain marker of the present invention, preferably BC2LCN or a modified product, is used together with means of the following (1) to (3) to make a kit or an apparatus, the kit or the apparatus acts as a kit or an apparatus capable of analyzing the undifferentiation sugar chain marker and thus may be a kit or an apparatus for determining the differentiation status of stem cells. The probe for detecting the undifferentiation sugar chain marker of the present invention is preferably used by immobilizing it on the substrate surface.

(1) A means for contacting the probe with a culture supernatant of stem cells; however, the means is optional because the means can be replaced by handwork.

(2) A fluorescent label for fluorescently labeling the probe for detection or the culture supernatant; as used herein, "fluorescently labeling the culture supernatant" means using a fluorescent substance (for example, "Cy3-NHS ester") capable of fluorescently labeling the undifferentiation sugar chain marker of the present invention as an object of detection in the culture supernatant, i.e., "a sugar chain structure represented by formula 1 or 2 or a substance containing the sugar chain structure".

(3) A means or an apparatus for detecting the fluorescent label.

Making a set of a substrate on which the probe for detecting the undifferentiation sugar chain marker of the present invention is immobilized and a means for labeling the protein immobilized on the substrate surface or culture supernatant provides a kit for determining the differentiation status of stem cells. Preferably, a means or an apparatus for contacting the culture supernatant of stem cells with the substrate surface may be made in a set therewith, and further, a means or an apparatus for detecting the fluorescent label may also be made in a set therewith. Particularly, the use of BC2LCN or a modified product as a probe for detecting the undifferentiation sugar chain marker provides a kit capable of highly sensitively determining the differentiation status of stem cells.

(4) Procedure of Measurement of Undifferentiation Sugar Chain Marker Using rBC2LCN The case of using rBC2LCN as the typical lectin of the present invention will be mainly described below. However, it is as described above that the present invention is not limited only to rBC2LCN.

(a) The culture supernatant labeled with "Cy3-NHS ester" or the like is directly reacted with a substrate in which rBC2LCN is immobilized on a glass slide to measure the binding therebetween using an evanescent wave excitation fluorescence detection system. In this case, the culture supernatant is sometimes used for analysis after physically or chemically concentrating it in advance.

(b) rBC2LCN immobilized on a substrate such as an ELISA plate, a magnetic bead, or a filter can also be reacted with the culture supernatant labeled with enzyme, fluorescence, biotin, or the like in advance to detect the binding therebetween using color development, light emission, fluorescence, or the like. Alternatively, after reaction with the culture supernatant, a labeled antibody or lectin capable of binding to a protein binding to rBC2LCN can also be reacted thereover. Particularly, more sensitive measurement can be performed by using "lectin-lectin sandwich method" (described later for details) using a lectin capable of binding to a protein binding to rBC2LCN.

(c) The culture supernatant can be reacted with an immobilized antibody or lectin capable of binding to the undifferentiation sugar chain marker of the present invention, followed by reacting rBC2LCN labeled with enzyme, biotin, fluorescence, or the like in advance, therewith. rBC2LCN is labeled with fluorescence, enzyme, biotin, or the like by an ordinary method and detected by a known method such as fluorescence staining, flow cytometry, ELISA, or lectin blotting. A variant in which a fluorescently labeled amino acid is introduced into a particular site of the sugar-binding domain of rBC2LCN can be prepared by using the known method of Hohsaka et al. for introducing a fluorescently labeled amino acid into any site in an amino acid sequence (see Non Patent Literature 6), or a conventional fluorescence resonance energy transfer (FRET) method or the chemically amplified luminescence proximity homogeneous assay method of PerkinElmer Co., Ltd. (http://www.perkinelmer.co.jp/products_ls/assays/assays_0010.html) in labeling rBC2LCN; thus, the differentiation degree of cells can be evaluated by simply mixing the rBC2LCN variant with the culture supernatant of cells.

(d) Because rBC2LCN is highly sensitive, when the culture supernatant is reacted with the substrate on which rBC2LCN is immobilized, it is possible to determine the presence or absence of the undifferentiation sugar chain marker "Fucα1-2Galβ1-3GlcNAc/GalNAc" of the present invention even at a picomolar (pM) or nanomolar (nM) level; thus, measurement can also be performed by collecting on the order of 0.1 to 10 μl of an aliquot of the culture supernatant of the culture medium during differentiation induction. Generally, measurement is preferably performed using the culture supernatant discarded in the medium replacement performed periodically (for example, daily).

(e) Measured values for only the medium having the same composition are generally used as a control in determining the differentiation degree of cells subjected to differentiation induction; however, in the case of accurate quantitative determination, it is preferable to use values for the culture supernatant of cells that are not subjected to differentiation induction.

5. Test Cell of Interest

The test cells of interest herein are "stem cells" in an undifferentiated state, or cells specifically differentiated into various tissues by the induction of differentiation of the stem cells. "Stem cells" here refers, in its broad sense, to cells in an undifferentiated state, and includes, for example, pluripotent stem cells (embryonic stem cells: ES cells), various somatic stem cells such as hematopoietic stem cells, neural stem cells and skin tissue stem cells as well as stem cells (iPS cells) obtained by introducing a gene expressed specifically in stem cells to somatic cells and the like for dedifferentiation. Stem cells including ES cells are considered to be controlled by a common mechanism in a substantial proportion of mammals as well as humans; thus, the stem cells of the present invention hold true also for the case of using stem cells derived from mammals other than humans, such as monkey, pig, cow, goat, sheep, mouse, and rat.

B. Method for Detecting Substance to Be Detected Having Sugar Chain

[General Outline]

Now will be described the method for detecting a substance to be detected having the sugar chain according to the present invention.

An attempt has been made to use a protein detected in a biological sample with affection with a disease, progress of disease, or the like, as a disease marker. The detection of a disease marker occurring in a biological sample such as blood, urine, or saliva enables the noninvasive determination of the presence of affection, the degree of progress, and the like and can aid early diagnosis of diseases, evaluation of a therapeutic effect, prognosis, and so on. It has previously been reported that glycoproteins such as mucin are specifically detected in various cancers. It has also been reported that the sugar chain structure of a particular glycoprotein varies depending on the type of cancer.

"Antibody-antibody sandwich method" involving putting a protein between two antibodies for detection has conventionally been known as a method for specifically detecting a protein, including a glycoprotein. In the antibody-antibody sandwich method, a desired protein is first separated specifically from a sample using a first antibody (capture antibody) capable of binding to the desired protein. A second antibody (detection antibody) capable of binding to the desired protein is then contacted with a complex of "capture antibody -desired protein" to form the complex of "capture antibody-desired protein-detection antibody". An antibody labeled with fluorescence or the like is used as the detection antibody, and the complex in the sample is detected by detecting the fluorescence or the like to detect the desired protein. In the antibody-antibody sandwich method, the two antibodies against the same antigen can be used to sensitively detect the desired protein with high specificity.

Because a sugar chain generally has low antigenicity, it is difficult to obtain an antibody capable of binding to only a protein having a particular sugar chain structure. Thus, the antibody-antibody sandwich method has a problem of being not suitable for the construction of a system for detecting the sugar chain of a glycoprotein. To perform the antibody-antibody sandwich method, it is necessary to obtain an antibody capable of specifically binding to a desired protein, and for that purpose, a purified product of the desired protein should be first obtained.

To solve the above problem, the present invention provides a method and a kit for detecting a substance to be detected having a sugar chain (hereinafter also referred to as "lectin-lectin sandwich method"), as described below.

[1] A method for detecting a substance to be detected having a sugar chain, comprising contacting the substance to be detected with lectin 1 and lectin 2 each having a binding property to the sugar chain to form a complex composed of the lectin 1, the substance to be detected, and the lectin 2, and detecting the complex, wherein at least one of the lectin 1 and the lectin 2 is a lectin having no sugar chain.

[2] The detection method according to [1] above, wherein the substance to be detected is a complex carbohydrate selected from the group consisting of glycoproteins, glycolipids, proteoglycans, glycopeptides, lipopolysaccharides, peptidoglycan, and glycosides in each of which a sugar chain binds to a steroid compound.

[3] The detection method according to [1] or [2] above, wherein the lectin 1 and the lectin 2 each have binding properties to sugar chain structures different from each other.

[4] The detection method according to any one of [1] to [3] above, wherein the lectin having no sugar chain is a recombinant lectin expressed in prokaryotic cells or a modified lectin obtained by modifying the sugar chain structure of a natural protein.

[5] The detection method according to any one of [1] to [4] above, comprising contacting the substance to be detected with the lectin 1 having no sugar chain and immobilized to an insoluble support and the lectin 2 not immobilized to an insoluble support to form the complex and detecting the complex.

[6] The detection method according to [5] above, wherein the method comprises a first procedure of contacting the substance to be detected with the lectin 1 having no sugar chain and immobilized to an insoluble support to obtain complex 1 composed of the lectin 1 and the substance to be detected, and a second procedure of contacting the complex 1 with the lectin 2 to obtain complex 2 composed of the lectin 1, the substance to be detected, and the lectin 2.

[7] The detection method according to any one of [1] to [6] above, wherein both of the lectin 1 and the lectin 2 are lectins having no sugar chain.

[8] A kit used for the detection of a substance to be detected having a sugar chain, comprising lectin 1 and lectin 2 each having a binding property to the sugar chain, wherein at least one of the lectin 1 and the lectin 2 is a lectin having no sugar chain.

[9] The kit according to [8] above, comprising an insoluble support, the lectin 1 having no sugar chain and immobilized to the insoluble support, and the lectin 2 not immobilized to the insoluble support.

[10] The kit according to [8] or [9] above, wherein both of the lectin 1 and the lectin 2 are lectins having no sugar chain.

Here, the terms will be described which are used in the lectin-lectin sandwich method and the like according to the present invention.

"Sugar chain" means a group of compounds each having a structure in which monosaccharides are linked to each other in a chain (straight chain or dendritically branched chain) form by glycosidic linkage. Monosaccharides constituting the sugar chain include hexoses such as glucose, galactose, and mannose; deoxyhexoses such as L-fucose; hexosamines such as N-acetylglucosamine and N-acetylgalactosamine; sialic acids such as N-acetylneuraminic acid and N-glycolylneuraminic acid; and pentoses such as xylose and L-arabinose. The number of monosaccharides constituting the "sugar chain" is not particularly limited and on the order of 2 to several tens of thousands.

"Lectin" means a protein recognizing the partial structure or the whole structure of the sugar chain binding to a complex carbohydrate such as a glycoprotein, a glycolipid, a proteoglycan, a glycopeptide, a lipopolysaccharide, peptidoglycan, and a glycoside of a steroid compound or the like, and binding thereto.

[Lectin-Lectin Sandwich Method]

The lectin-lectin sandwich method according to the present invention will be described below. The lectin-lectin sandwich method comprises "complex formation procedure" and "detection procedure". The "complex formation procedure" is a procedure involving contacting a substance to be detected having a sugar chain with lectin 1 and lectin 2 each having a binding property to the sugar chain to form a complex composed of the lectin 1, the substance to be detected, and the lectin 2 (the complex of "lectin 1-substance to be detected-lectin 2"). The "detection procedure" is a procedure involving detecting the substance to be detected by detecting the complex of "lectin 1-substance to be detected-lectin 2" formed in the complex formation procedure.

In the lectin-lectin sandwich method according to the present invention, the "substance to be detected" may be any substance having a sugar chain (hereinafter also referred to as "complex carbohydrate") and is considered to be specifically a glycoprotein, a glycolipid, a proteoglycan, a glycopeptide, a lipopolysaccharide, peptidoglycan, a glycoside in which a sugar chain binds to a steroid compound or the like, and the like.

In the lectin-lectin sandwich method according to the present invention, examples of the "sample" capable of containing the substance to be detected include, but not limited to, materials of biological origin, such as blood, serum, plasma, urine, saliva, lymph, spinal fluid, pleural effusion, ascitic fluid, and lacrimal fluid.

[Lectin 1 and Lectin 2]

The lectin 1 and the lectin 2 used in the complex formation procedure each recognize the partial structure or the whole structure of the sugar chain of a substance to be detected and bind (have a binding property) thereto. The sugar chain structure recognized by the lectin 1 and the sugar chain structure recognized by the lectin 2 may be the same; however, they are preferably different from each other. The lectin 1 and the lectin 2 binding to different sugar chain structures can be used to increase the specificity of detecting the substance to be detected.

The lectin 1 may be a single lectin or may be a mixture of a plurality of types of lectins. This is ditto for the lectin 2. When the mixture of a plurality of types of lectins is used as the lectin 1, the sugar chain structures recognized by the lectins contained in the mixture may be the same or different. This is ditto for the lectin 2.

Here, a lectin itself, by nature, has a sugar chain; however, this procedure uses a lectin having no sugar chain as at least one of the lectin 1 and the lectin 2. More preferably, lectins having no sugar chain are used as both of the lectin 1 and the lectin 2.

As a result of studies by the present inventors, it has been demonstrated that the use of lectins each having a sugar chain as the lectin 1 and the lectin 2 increases the background in detecting the complex of "lectin 1-substance to be detected-lectin 2" and does not enable sensitive detection. As a factor responsible for the increased background, the present inventors have assumed the potential formation of a complex in which the lectins 1 bind to the sugar chains of each other, a complex in which the lectins 2 bind to the sugar chains of each other, or a complex in which the lectin 1 and the lectin 2 bind the sugar chains of each other. Then, the present inventors attempted to suppress the formation of these complexes by using lectins having no sugar chain as the lectin 1 and/or the lectin 2, which has been found to enable the detection of the complex of "lectin 1-substance to be detected-lectin 2" with good sensitivity.

In other words, the use of lectins having no sugar chain as both of the lectin 1 and the lectin 2 has been demonstrated to enable the elimination of the formation of a complex of the lectins 1, a complex of the lectins 2, and a complex of the lectin 1 and the lectin 2 and the sensitive detection of the complex of "lectin 1-substance to be detected-lectin 2" only. The use of a lectin having no sugar chain as one of the lectin 1 and the lectin 2 also enables the suppression of the formation of a complex of the lectins 1, a complex of the lectins 2, and a complex of the lectin 1 and the lectin 2 and the detection of the complex of "lectin 1-substance to be detected-lectin 2" only with good sensitivity.

Here, the "lectin having no sugar chain" is intended to encompass lectins having no sugar chains capable of causing the binding of the lectins to each other via the sugar chains in addition to a lectin having no glycosylation. More specifically, as the "lectin 1 having no sugar chain" can be used a lectin that does not have glycosylation with a sugar chain having the sugar chain structure recognized by the lectin 1 and/or a sugar chain having the sugar chain structure recognized by the lectin 2. This is because when the lectin 1 has a sugar chain but contains no sugar chain structure recognized by the lectin 1 and/or the lectin 2 in the sugar chain, a complex of the lectins 1 and/or a complex of the lectin 1 and the lectin 2 is not formed. Similarly, the "lectin 2 having no sugar chain" can be used if it is a lectin that does not have glycosylation with a sugar chain having the sugar chain structure recognized by the lectin 1 and/or a sugar chain having the sugar chain structure recognized by the lectin 2.

Specific examples of the lectin having no sugar chain include a recombinant lectin expressed in prokaryotic cells, and a modified lectin obtained by modifying the sugar chain structure of a natural protein.

[Recombinant Lectin]

Because prokaryotic cells does not have a membrane structure for glycosylating a protein synthesized in the cell, a recombinant lectin expressed using prokaryotic cells as host cells has no sugar chain. As will be described below, the recombinant lectin can be simply bulk-produced at low cost using a conventional genetic engineering method.

To explain an example of a method for producing a recombinant lectin, into a suitable expression vector is first incorporated a base sequence containing the base sequence encoding the amino acid sequence of a lectin having a binding property to a desired sugar chain structure according to an ordinary method to provide a recombinant vector for expression. Into the expression vector may be incorporated a base sequence containing only the base sequence encoding the amino acid sequence of the sugar chain binding portion of the amino acid sequences of a lectin having a binding property to a desired sugar chain structure.

The expression vector is not particularly limited provided that it is a vector expressing a recombinant lectin in various host cells and having the function of producing the recombinant lectin. Examples of the expression vector include a plasmid vector, a phage vector, and a virus vector. Specific examples thereof include plasmid vectors such as pTrcHis2 vector, pcDNA3.1/myc-His vector (from Invitrogen Co., Ltd.), pUC119 (from Takara Shuzo Co., Ltd.), pBR322 (from Takara Shuzo Co., Ltd.), pBluescript II KS+ (from Stratagene Corporation), Pqe-tri (from Qiagen Co., Ltd.), pET, pGEM-3Z, pGEX, and pMAL; bacteriophage vectors such as λENBL3 (from Stratagene Corporation) and λDASHII (from Funakoshi Co., Ltd.); and cosmid vectors such as Charomid DNA (from Wako Pure Chemical Industries Ltd.) and Lorist6 (from Wako Pure Chemical Industries Ltd.). Also included are *Escherichia coli*-derived plasmids (for example, pTrc99A, pKK223, and pET3a), bacteriophages such as λphage as well as pA1-11, pXT1, pRc/CMV, pRc/RSV, pcDNA I/Neo, p3xFLAG-CMV-14, pCAT3, pcDNA3.1, and pCMV.

To facilitate the detection and purification of a recombinant lectin, the lectin may be expressed as a fusion protein with a tag peptide or another protein. Examples of the tag peptide to be fused include FLAG tags, 3XFLAG tags, and His tags (for example, 6×His tag).

Then, suitable host cells are transformed (transduced) using the resultant recombinant expression vector to prepare a transformant. As host cells are used cells capable of expressing and producing a recombinant protein without glycosylation. Examples of the host cells include prokaryotic organisms, specifically *Escherichia coli*. and bacteria of the genus *Bacillus* (*B. subtilis, B. brevis, B. borstelenis*, and the like). Examples of the *Escherichia coli*. which can be used include BL21, BL21(DE3), K-12, DH1, DH5, DH5α, M15, HB101, C600, XL-1 Blue, JM109, JM105, JM127, XL1-Blue, VCS257, and TOP10. Competent cells may also be used, which have a higher efficiency of introduction of plasmid or phage DNA. Examples of the competent cells include *E. coli* DH5α Competent Cell and *E. coli* JM109 Competent Cells (from Takara Bio Co., Ltd.).

The transformation of host cells with the recombinant expression vector can be performed using a heretofore known method. For example, when the host cells are *Escherichia coli*, it can be performed using the method of Cohen et al. (see Proc. Natl. Acad. Sci. U.S.A., (1972) 9, 2110), a protoplast method (see Mol. Gen. Genet., (1979) 168, 111), a competent method (see J. Mol. Biol., (1971) 56, 209), the method of M. Morrison (see Method in Enzymology, 68, 326-331, 1979), or the like. When commercial competent cells are used, transformation may be performed according to the product protocol.

To confirm that the transformant (transductant) expresses and produces a recombinant lectin, an ordinary method can be applied which uses hybridization, such as southern hybridization or colony hybridization, with a probe. The following methods can also be adopted.

When the recombinant lectin is not secreted into a culture medium of the transformant, for example, when it is expressed as a transmembrane-type protein, the resultant transformant is treated by an ordinary method involving destroying or dissolving cells (for example, subjecting to sonication, treating with a homogenizer or the like, or treating with a suitable membrane-dissolving agent such as a surfactant) to provide a lysate thereof. Then, if necessary, after the protein in the lysate is further purified, the presence of the expressed tag peptide in the lysate is confirmed, for example, by performing a conventional immunological measurement method using an antibody to the tag peptide (a dot western blotting method, a western blotting method, or the like).

When the recombinant lectin is secreted into the culture medium of the transformant, the culture medium (culture supernatant) is subjected to the same confirmation procedure as that for the above lysate.

The transformant is cultured in a nutrient medium to form a recombinant lectin. The culture is performed by a heretofore known method, and the temperature, medium, pH, and culture time can also be properly set. The culture of the transformant for which host cells are *Escherichia coli*. may be performed in a liquid medium typically used under conditions for an ordinary method of culturing *Escherichia coli*.

The recombinant lectin can be obtained from a culture obtained by culture as follows. That is, when the recombinant lectin is present in the periplasm or cytoplasm of the transformant, bacterial cells or cells are recovered from the culture by a method such as filtration or centrifugation and resuspended in a suitable buffer solution. Then, the cell wall and/or cell membrane of the recovered cells or the like is destroyed by a method such as surfactant treatment, sonication, lysozyme treatment, or freeze and thawing, followed by obtaining a crude extract containing the recombinant lectin by a method such as centrifugation or filtration. When the recombinant lectin is secreted into a culture medium of the transformant, the culture medium (culture supernatant) is obtained. Then, according to a conventionally used method, the recombinant lectin is isolated and purified from the crude extract or the culture medium (culture supernatant) so that it is not contaminated with saccharides (sugar chain).

Methods for the isolation or purification of the recombinant lectin include, for example, a method using solubility, such as salting-out or a solvent precipitation method, a method using a difference in molecular weight, such as dialysis, ultrafiltration, gel filtration, or sodium dodecyl sulfate-polyacrylamide gel electrophoresis, a method using electric charge, such as ion-exchange chromatography, a method using specific affinity, such as affinity chromatography, a method using a difference in hydrophobicity, such as reversed-phase high-performance liquid chromatography, and a method using a difference in isoelectric point such as isoelectric focusing electrophoresis. The purified recombinant lectin can be confirmed, for example, by ELISA using an anti-His antibody, or the like.

[Modified Lectin]

The modified lectin can be obtained by treating a natural lectin with acid or glycolytic enzyme.

The natural lectin can be treated with periodic acid or a salt thereof (a sodium salt, a potassium salt, or the like) or an acid such as trifluoromethane sulfonic acid to oxidize the hydroxyl group of the sugar chain to change the whole structure of the sugar chain or a partial structure in the sugar chain. The sugar chain structure can be removed by β decomposition by alkali treatment. This can alter a sugar chain structure recognizable by the natural lectin or a sugar chain structure recognized by another lectin present in the sugar chain of the natural lectin to convert the natural lectin to a modified lectin that does not cause the binding of lectins to each other via the sugar chain. The acid treatment may be performed by a heretofore known method (see also Example 11 to be described later).

The sugar chain can be removed from a natural lectin by treating the natural lectin with a glycolytic enzyme such as glycanase (N-glycanase, O-glycanase, or the like), mannosidase, galactosidase, keratanase, chondroitinase, sialidase, fucosidase, N-acetylglucosaminidase, or N-acetylhexosaminidase. Alternatively, the sugar chain of a natural lectin can be cut by glycolytic enzyme treatment to change the whole structure of the sugar chain or a partial structure in the sugar chain. These can alter a sugar chain structure recognized by a natural lectin or a sugar chain structure recognized by another lectin present in the sugar chain of the natural lectin to convert the natural lectin to a modified lectin that does not cause the binding of lectins to each other via the sugar chain. The enzyme treatment may be performed by a heretofore known method (see also Example 11 to be described later).

In the modified lectin obtained by the acid treatment, alkali treatment, or glycolytic enzyme treatment, the binding property thereof to the sugar chain is sometimes lost or weakened by albuminoid degeneration. Thus, it is preferable to use recombinant lectins as described above as the lectin 1 and lectin 2 used in the complex formation procedure. The recombinant lectin is preferable also because it can be simply bulk-produced with low cost.

[Complex Formation Procedure]

When a substance to be detected is contacted with the lectin 1 and the lectin 2 in the complex formation procedure, the lectin 1 and the lectin 2 may be simultaneously or sequentially reacted with a sample. The complex formation procedure may be performed using a heterogeneous method involving performing B/F separation using an insoluble support, or may be performed using a homogeneous method involving not performing the B/F separation.

The amounts (concentrations) of the lectin 1 and lectin 2 reacted with the sample are properly set depending on the type of the substance to be detected, the necessary measurement sensitivity, the measurement method, the measuring apparatus, and the like.

The method for performing B/F separation using an insoluble support is carried out, for example, by contacting a substance to be detected with the lectin 1 immobilized to the insoluble support and the free lectin 2 that is not immobilized to the insoluble support to form a complex. More specifically, the method for performing B/F separation is carried out by a first procedure of contacting a substance to be detected with the lectin 1 immobilized to an insoluble support to provide complex 1 composed of the lectin 1 and the substance to be detected and a second procedure of contacting the complex 1 with the free lectin 2 to provide complex 2 composed of the lectin 1, the substance to be detected, and the lectin 2, On this occasion, a lectin having no sugar chain is preferably used as the lectin 1 immobilized to the insoluble support, and lectins having no sugar chain are more preferably used as both of the lectin 1 and the lectin 2. Here, although an example of immobilizing the lectin 1 to an insoluble support has been described, the lectin 2 can naturally be immobilized to the insoluble support; in this case, a lectin(s) having no sugar chain is used preferably as the lectin 2, more preferably as both of the lectin 2 and the lectin 1.

For the insoluble support for B/F separation can be used a substrate used in a conventional method for immobilizing proteins, such as a glass slide, an ELISA plate, a magnetic bead, a filter, a film, or a membrane. As a material for the substrate is used glass, silicon, polycarbonate, polystyrene, polyurethane, or the like.

The method for immobilizing a lectin on an insoluble support is not particularly limited, and known methods can be applied, such as a chemical binding method (a method involving immobilization by covalent binding) and a physical adsorption method. It is also possible to immobilize a lectin on the insoluble support using an extremely strong binding reaction such as avidin-biotin reaction. In this case, a biotinylated lectin in which biotin is bound to a lectin may be immobilized on a streptoavidin plate on which streptoavidin is coated. A lectin may also be immobilized on the insoluble support via any of the various linkers conventionally used in the art.

In the method for performing B/F separation using an insoluble support, after the first procedure of reacting a sample with the lectin 1 immobilized on the insoluble support, a washing procedure for removing unnecessary substances from the solid phase surface may be included before performing the second procedure of reacting the complex 1 (insoluble support-lectin 1-substance to be detected) with the free lectin 2. After the second procedure, the washing procedure may be included before performing a detection procedure. The washing procedure can remove contaminants in the sample and the unreacted lectin 2 from the solid phase surface to separate only the complex 2 (insoluble support-lectin 1-substance to be detected-lectin 2) on the solid phase surface.

In the method without performing B/F separation, as a method for separating a complex of the lectin 1, the substance to be detected, and the lectin 2 can be applied, for example, a chromatography method, a high-performance liquid chromatography method, an electrophoresis method, a capillary electrophoresis method, a capillary chip electrophoresis method, a method using an automated immunological analyzer such as, for example, LiBASys (from Shimadzu Corporation). Concrete conditions are properly set depending on the sample, the substance to be detected, and the type and properties of the lectin 1 and the lectin 2. For example, the separation using HPLC may be performed according to Anal. Chem. 65, 5, 613-616 (1993), Patent Literature 1, or the like. The separation using a capillary electrophoresis method may be performed according to J. Chromatogr. 593, 253-258 (1992), Anal. Chem. 64 1926-1932 (1992), Patent Literature 2, or the like. The separation using, for example, LiBASys as an automated immunological analyzer may be performed according to a method as described in Journal of Analytical Bio-Science 22 (4), 303-308 (1999).

As described above, in this procedure, lectins having no sugar chain can be used as both of the lectin 1 and the lectin 2 to selectively form only the complex of "lectin 1-substance to be detected-lectin 2" without the formation of a complex of the lectins 1, a complex of the lectins 2, and a complex of the lectin 1 and the lectin 2. A lectin having no sugar chain can also be used as one of the lectin 1 and the lectin 2 to selectively form the complex of "lectin 1-substance to be detected-lectin 2" by suppressing the formation of a complex of the lectins 1, a complex of the lectins 2, and a complex of the lectin 1 and the lectin 2.

[Detection Procedure]

The complex of "lectin 1-substance to be detected-lectin 2" formed in the complex formation procedure can be detected, for example, by a method using a labeling substance. Examples of the labeling substance include all labeling substances conventionally used in the art, including enzymes used in conventional immunoassay methods and the like, radioisotopes, fluorescent substances, luminescent substances, substances having absorption in the ultraviolet region, and substances each having a property as a spin labeling agent.

The binding of a labeling substance to the lectin 1 and/or the lectin 2 may be performed, for example, by properly using a labeling method taking place in conventional immunoassay methods and the like. A method can also be adopted which involves binding a labeling substance to a lectin via one or several amino acids or via one or several amino acids and a linker. In addition, because various kits for binding the labeling substance to a protein are commercially available, they may each be used to perform labeling according to the instruction manual included with the kit.

The detection and measurement of the complex are performed according to the respective predetermined methods depending on properties detectable by some method, which the labeling substance has. For example, a method for performing B/F separation using the lectin 1 immobilized on the insoluble support and the free lectin 2 labeled with horseradish peroxidase (HRP) as a labeling substance is roughly as follows.

That is, a sample containing a substance to be detected having a sugar chain is contacted with an insoluble support having the immobilized lectin 1 for reaction at 4 to 40° C. for 3 minutes to 20 hours to form complex 1 of the lectin 1 and the substance to be detected on the solid phase surface. Then, a solution containing the lectin 2 labeled with HRP is added to the solid phase surface for reaction at 4 to 40° C. for 3 minutes to 16 hours to form complex 2 of the immobilized lectin 1-substance to be detected-labeled lectin 2. Subsequently, a suitable concentration of TMB (3,3'5,5'-tetramethylbenzidine) solution is added thereto and reacted for a predetermined time. Thereafter, a reaction termination solution such as 1 M sulfuric acid is added thereto to stop the reaction, followed by measuring absorbance at 450 nm. The amount of the substance to be detected in the sample can be determined from the resultant measured value and the standard curve obtained by performing the same measurement for known concentrations of a solution of the substance to be detected in advance.

Using the lectin 1 labeled, for example, with Alexa Fluor-488 tetrafluorophenyl ester and the lectin 2 labeled, for example, with Alexa Fluor-647 succinimidyl ester, the substance to be detected can also be measured according to the well-known fluorescence correlation spectroscopy (FCCS).

The complex of "lectin 1-substance to be detected-lectin 2" can also be detected, for example, by a measurement method using a property originating from the complex, specifically a method such as a homogeneous immunoassay system (e.g., surface plasmon resonance), without using a labeling substance.

As described above, only the complex of "lectin 1-substance to be detected-lectin 2" can be sensitively detected in this procedure by using lectins having no sugar chain for both of the lectin 1 and the lectin 2 in the complex formation procedure. The complex of "lectin 1-substance to be detected-lectin 2" can also be detected with good sensitivity in this procedure by using a lectin having no sugar chain for one of the lectin 1 and the lectin 2 in the complex formation procedure.

[Example Embodiments]

Specific examples of embodiments of the lectin-lectin sandwich method will be described below. In this respect, operations (washing and the like) of removing undesired substances may be performed after each operation, if necessary.

(1-1) Method 1 Using Lectin 1 Immobilized on Insoluble Support and Free Non-labeled Lectin 2 Not Immobilized on Insoluble Support (i) A sample is contacted with lectin 1 immobilized on an insoluble support and free non-labeled lectin 2 to form a complex of the lectin 1 immobilized on an insoluble support, a substance to be detected, and the non-labeled lectin 2, (ii) the amount of the complex is measured, and (iii) the amount of the substance to be detected in the sample is measured based on the resultant amount of the complex.

(1-2) Method 2 Using Lectin 1 Immobilized on Insoluble Support and Free Non-labeled Lectin 2

(i) A sample is contacted with lectin 1 immobilized on an insoluble support to form complex 1 of the lectin 1 immobilized on an insoluble support and a substance to be detected, (ii) the complex 1 is then contacted with free non-labeled lectin 2 to form complex 2 of the complex 1 and the non-labeled lectin 2, (iii) the amount of the complex 2 is then measured, and (iv) the amount of the substance to be detected in the sample is measured based on the amount of the complex 2.

(2-1) Method 1 Using Lectin 1 Immobilized on Insoluble Support and Free Lectin 2 Labeled with Labeling Substance (i) A sample is contacted with lectin 1 immobilized on an insoluble support and free lectin 2 labeled with a labeling substance to form a complex of the lectin 1 immobilized on an insoluble support, a substance to be detected, and the labeled lectin 2, (ii) the amount of the labeling substance in the complex is measured, and (iii) the amount of the substance to be detected in the sample is measured based on the resultant amount of the labeling substance.

(2-2) Method 2 Using Lectin 1 Immobilized on Insoluble Support and Free Lectin 2 Labeled with Labeling Substance (i) A sample is contacted with lectin 1 immobilized on an insoluble support to form complex 1 of the lectin 1 immobilized on an insoluble support and a substance to be detected, (ii) the complex 1 is then contacted with free lectin 2 labeled with a labeling substance to form complex 2 of the complex 1 and the labeled lectin 2, (iii) the amount of the labeling substance in the complex 2 is then measured, and (iv) the amount of the substance to be detected in the sample is measured based on the resultant amount of the labeling substance.

(3-1) Method 1 Using Free Lectin (i) A sample is contacted with free lectin 1 and free lectin 2 to form a complex of the lectin 1, a substance to be detected, and the lectin 2, (ii) the amount of the complex is measured, and (iii) the amount of the substance to be detected in the sample is measured based on the resultant amount of the complex.

(3-2) Method 2 Using Free Lectin (i) A sample is contacted with free lectin 1 to form complex 1 of a substance to be detected and the lectin 1, (ii) the complex 1 is then contacted with free lectin 2 to form complex 2 of the lectin 1, the substance to be detected, and the lectin 2, (iii) the amount of the complex 2 is then measured, and (iv) the amount of the substance to be detected in the sample is measured based on the resultant amount of the complex 2.

(4-1) Method 1 Using Free Lectin 1 and Free Lectin 2 Labeled with Labeling Substance (i) A sample is contacted with free lectin 1 and free lectin 2 labeled with a labeling substance to form a complex of the lectin 1, a substance to be detected, and the lectin 2, (ii) the amount of the labeling substance in the complex is then measured, and (iii) the amount of the substance to be detected in the sample is measured based on the resultant amount of the labeling substance.

(4-2) Method 2 Using Free Lectin 1 and Free Lectin 2 Labeled with Labeling Substance (i) A sample is contacted with free lectin 1 to form complex 1 of a substance to be detected and the lectin 1, (ii) the complex 1 is then contacted with free lectin 2 labeled with a labeling substance to form complex 2 of the complex 1 and the labeled lectin 2, (iii) the amount of the labeling substance in the complex 2 is then measured, and (iv) the amount of the substance to be detected in the sample is measured based on the resultant amount of the labeling substance.

(5-1) Method 1 Using Free Lectin 1 Labeled with Labeling Substance and Free Lectin 2 Labeled with Labeling Substance (i) A sample is contacted with free lectin 1 labeled with a labeling substance and free lectin 2 labeled with a labeling substance to form a complex of the labeled lectin 1, a substance to be detected, and the labeled lectin 2, (ii) the amount of the labeling substance in the complex is then measured, and (iii) the amount of the substance to be detected in the sample is measured based on the resultant amount of the labeling substance.

(5-2) Method 2 Using Free Lectin 1 Labeled with Labeling Substance and Free Lectin 2 Labeled with Labeling Substance (i) A sample is contacted with free lectin 1 labeled with a labeling substance to form complex 1 of a substance to be detected and the labeled lectin 1, (ii) the complex 1 is then contacted with free labeled lectin 2 labeled with a labeling substance to form complex 2 of the complex 1 and the labeled lectin 2, (iii) the amount of the labeling substance in the complex 2 is then measured, and (iv) the amount of the substance to be detected in the sample is measured based on the resultant amount of the labeling substance.

[Advantageous Effect of Lectin-Lectin Sandwich Method]

According to the lectin-lectin sandwich method described above, for example, when a glycoprotein is detected as a complex carbohydrate, if the glycoprotein has a plurality of sugar chains, a plurality of lectins capable of reacting with the sugar chains can be bound to the glycoprotein. Even when the glycoprotein has only one sugar chain, if a plurality of structures with which lectins can react are present in the one sugar chain, a plurality of the lectins can be bound to the glycoprotein. In contrast, in a conventional antibody-antibody sandwich method, only one antibody can be bound to one epitope of a glycoprotein. Thus, according to the lectin-lectin sandwich method, the detection sensitivity for a glycoprotein can be markedly increased compared to that according to the antibody-antibody sandwich method.

Even when because it is difficult to obtain an antibody binding only to a glycoprotein having a particular sugar chain structure, a detection system using the antibody-antibody sandwich method cannot be constructed, according to the lectin-lectin sandwich method, a detection system can be easily constructed using lectins capable of reacting with the sugar chain structure. In addition, in the lectin-lectin sandwich method, use of recombinant proteins as lectins enables the construction of a low-cost detection system.

Recent studies have showed various functions of sugar chains. It has become clear that sugar chains play noticeable and important roles particularly in cancer (metastasis, tumor markers, and the like), immunity (immunoreceptor regulation, immunocyte differentiation, antibody drug, and the like), fertilization, development/differentiation (regenerative medicine, and the like), infection (influenza, *Helicobacter pylori*, cholera toxin, and the like), biopharmaceuticals, brain, blood groups, and the like. Thus, the lectin-lectin sandwich method of the present invention capable of detecting a particular sugar chain structure is especially effectively used, for example, in the fields of the studies (discovery/development and the like) of disease-associated biomarkers such as cancer markers (SLX antigen, CA19-9 antigen, and the like), the diagnosis/determination of cancers and other diseases by detecting the biomarkers (for example, determination of malignancy of cancers, evaluation of cancer metastasis, and the like), the elucidation of the pathogenic mechanism of diseases and the development of therapeutic methods, the studies of mesenchymal stem cell markers/differentiation markers and the like, the quality control of biopharmaceuticals and the development thereof, and the quality control of cells.

The lectin-lectin sandwich method according to the present invention is not limited to a manual means and can also be applied to a measurement system using an automated analyzer for easy and rapid measurement. The combination of reagents or the like when measurement is performed by a manual means or an automated analyzer is not particularly limited; in accordance with the circumstance and model of the automated analyzer applied or taking into consideration other factors, a combination of reagents or the like deemed best may be properly selected and used. In addition, the lectin-lectin sandwich method according to the present invention can also be applied to Micro-TAS (Micro-Total Analysis Systems: μ-TAS, μ comprehensive analysis system).

[Specific Example]

The lectin-lectin sandwich method will be described below in further detail taking, for example, a case where the above undifferentiation sugar chain marker in a culture supernatant of stem cells is detected as a complex carbohydrate. Here, with reference to FIG. 1, will be described below a method according to "(2-2) Method 2 Using Lectin 1 Immobilized on Insoluble Support and Free Lectin 2 Labeled with Labeling Substance" in the above example embodiments.

(a) First Procedure of Complex Formation Procedure

The culture supernatant is first contacted with solid phase surface S (see FIG. 1-A) of an insoluble support on which recombinant BC2LCN (hereinafter also referred to as "rBC2LCN") is immobilized as lectin $L_1$, for reaction. rBC2LCN has a binding property to sugar chain structure $G_1$ (Fucα1-2Galβ1-3GlcNAc/GalNAc) of a differentiated sugar chain marker represented by the formula 1 or 2, contained as substance to be detected T in the culture supernatant. Thus, on the solid phase surface S after reaction is formed complex 1 in which the lectin $L_1$ binds to the substance to be detected T via the sugar chain structure $G_1$ (see FIG. 1-B).

The lectin $L_1$ preferably has high specificity to the sugar chain structure $G_1$ of the substance to be detected T. In this regard, rBC2LCN has high specificity to the sugar chain structure "Fucα1-2Galβ1-3GlcNAc/GalNAc". Thus, this procedure can specifically capture the undifferentiation sugar chain marker in the culture supernatant on the solid phase surface S by the specific binding between the lectin $L_1$ and the sugar chain structure $G_1$.

rBC2LCN, having no sugar chain, can be used as the lectin $L_1$ in this procedure to prevent the formation of a complex of the lectin $L_1$ and lectin $L_2$ in a second procedure to be described next.

(b) Second Procedure of Complex Formation Procedure

Free lectin $L_2$ labeled with a fluorescent substance or the like is then contacted with the complex 1 formed on the solid phase surface S for reaction. As a preprocedure, washing may be performed for removing contaminants present on the solid phase surface S.

As the lectin $L_2$ is used SRL, CGL2, ABA, or XCL shown to have a binding property to the undifferentiation sugar chain marker (see Example 6). The amino acid sequences of these lectins are shown in SEQ ID NOS: 2 to 5. In the Sequence Listing, SEQ ID NO: 2 represents the amino acid sequence of ABA; SEQ ID NO: 3, the amino acid sequence of XCL; SEQ ID NO: 4, the amino acid sequence of SRL; and SEQ ID NO: 5, the amino acid sequence of CGL2. These lectins may be used in a combination of two or more thereof. In the figure, at $G_2$ is indicated the sugar chain structure bound by any of these lectins among the sugar chain structures of the undifferentiation sugar chain marker.

SRL, CGL2, ABA, and XCL are not required to have the whole lengths thereof corresponding to SEQ ID NOS: 2 to 5 provided that they maintain the property of specifically recognizing the undifferentiation sugar chain marker, and some amino acids may be partially deleted, substituted, inserted, or added in each of SEQ ID NOS: 2 to 5.

This procedure results in the formation of complex 2 in which the lectin $L_2$ further binds via the sugar chain structure $G_2$ to the complex 1 in which the lectin $L_1$ binds to the substance to be detected T via the sugar chain structure $G_1$ (see FIG. 1-C).

rBC2LCN, having no sugar chain, can be used as the lectin $L_1$ in the above first procedure to prevent the formation of a complex due to the binding of the lectin $L_2$ to the sugar chain of the lectin $L_1$ in this procedure, enabling the selective formation of only the complex 2 composed of rBC2LCN, the undifferentiation sugar chain marker, and the lectin $L_2$ on the solid phase surface S.

In addition, rSRL, rCGL2, rABA, or rXCL, having no sugar chain, can be used also as the lectin $L_2$ to prevent the formation of a complex due to the binding of the lectin $L_1$ to the sugar chain of the lectin $L_2$ and the formation of a complex of lectins $L_2$.

(c) Detection Procedure

Finally, the labeling substance labeled on the lectin $L_2$ is detected by a detection method depending on the property of the labeling substance, such as fluorescence detection, to detect the complex 2 formed on the solid phase surface S. Recombinant lectins having no sugar chain can be used as both of the lectin $L_1$ and the lectin $L_2$ in the complex formation procedure to sensitively detect only the complex 2 in this procedure.

In addition, the amount of the labeling substance may be measured by the measurement of fluorescence intensity or the like to measure the amount of the undifferentiation sugar chain marker in the culture supernatant based on the resultant amount of the labeling substance. As a preprocedure, washing may be performed for removing contaminants and the unreacted lectin $L_2$ present on the solid phase surface S.

In this specific example, the sandwich method can be performed using a combination of rBC2LCN (lectin $L_1$), and rSRL, rCGL2, rABA, and/or rXCL (lectin $L_2$) capable of binding to different sugar chain structures to enhance the specificity of detecting the undifferentiation sugar chain marker compared to when the detection is performed using only rBC2LCN.

According to this specific example, the sandwich method can be performed using labeled rSRL, rCGL2, rABA, and/or rXCL (lectin $L_2$) to provide a high detection signal compared to when the detection is performed using only labeled rBC2LCN (lectin $L_1$) or when a labeled sample is detected using only rBC2LCN. Thus, according to this specific example, more accurate quantification can be made in quantitatively detecting the undifferentiation sugar chain marker based on the intensity of the detection signal (see Example 7).

[Kit]

The kit used for the detection of a substance to be detected having a sugar chain according to the present invention comprises lectin 1 and lectin 2 each having a binding property to the sugar chain, wherein at least one of the lectin 1 and the lectin 2 is a lectin having no sugar chain.

A preferable aspect of the features and specific example of the kit are as described in the above explanation of the lectin-lectin sandwich method. Preferable aspects of the concentration and the like of these reagents may also be properly selected from the concentration range conventionally used in the art.

Reagents included in the kit may include reagents conventionally used in the art, such as, for example, a buffering agent, a reaction accelerator, saccharides, a protein, salts, a stabilizer (e.g., surfactant), and a preservative, which neither inhibit the stability of coexisting reagents and the like nor inhibit the reaction of the substance to be detected with the lectin 1 and the lectin 2. The concentration may also be properly selected from the concentration range conventionally used in the art.

In addition, the kit may include a standard used for preparing a standard curve for the substance to be detected. The standard used may be a commercially available substance or a substance produced according to a known method.

The terms and concepts according to the present invention are based on the meanings of the terms idiomatically used in the art, and various techniques used for practicing the present invention can be easily and positively performed by one of ordinary skill in the art based on known literature and the like, particularly except for the techniques whose written sources are acknowledged.

Various analyses and the like were performed in line with methods as described in the instruction manuals, catalogs, or the like of the analyzers, reagents, or kits used.

Reference shall be made as the contents of description of the present invention to the contents described in the technical references, patent publications, and patent application specifications cited herein.

EXAMPLES

The present invention will be described below in detail with reference to Examples. However, the present invention is not intended to be limited thereto.

In each Example, cells were cultured while daily replacing the medium with a fresh culture medium. Each detection was performed using the culture medium to be discarded obtained in the medium replacement, that is, using the culture supernatant of the culture medium after a lapse of 24 hours after medium replacement with the fresh culture medium.

Example 1

Cell Staining of ES Cell

ES cells (KhES1 strain) used in this Example were obtained from Stem Cell Research Center, Institute for Frontier Medical Sciences, Kyoto University. These cells were cultured by the method of Suemori et al. (see Non Patent Literature 4). Cells were fixed with 4% paraformaldehyde and washed with PBS, to which rBC2LCN fluorescently labeled (bound to Cy3) was then added for reaction at room temperature for 1 hour (the left middle stage in FIG. 2; the right shows the stained nuclei of the same cells.).

Figure 2:
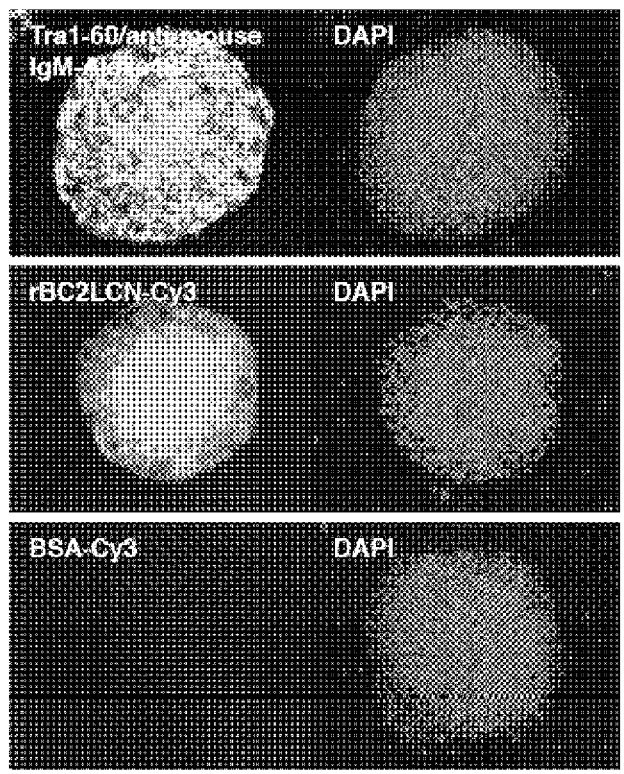
FIG. 2 is a set of photographs of undifferentiated ES cells (KhES1 strain) stained with Cy3-labeled rBC2LCN and Tral-60 (Example 1). Cy3-labeled BSA was reacted as a negative control. To identify the presence of cells, nuclear staining with DAPI was performed in each case.

As a target for comparison, in the left upper stage in FIG. 2 is shown the stained image of a colony obtained by reacting a KhES1 cell colony with Tra1-60 antibody capable of specifically recognizing ES cells and iPS cells and then further reacting anti-mouse IgM-Alexa488 as a secondary antibody therewith. The right upper stage shows the nuclei of the same cells stained with DAPI.

Fluorescently labeled rBC2LCN stains ES cells strongly like Tra1-60 antibody (the left middle stage in FIG. 2; the right shows the stained nuclei of the same tissue.). No fluorescence is observed when fluorescently labeled BSA is used as a negative control (the left lower stage in FIG. 2; the right shows the stained nuclei of the same cells.), showing that rBC2LCN strongly detects ES cells to the same or more extent than Tra1-60 antibody.

Because the above experiment is performed without crushing cells, it is noted that the sugar chain structure "Fucα1-2Galβ1-3GlcNAc/GalNAc" recognized by rBC2LCN, as a glycoprotein antigen on the cell surface is recognized by Tra1-60 antibody, is present as a constituent sugar of a glycoprotein and a glycolipid abundantly expressed on the surface of stem cells in an undifferentiated state so as to cover the cell surface.

Example 2

Staining of ES Cell in Differentiation Induction Thereof

Figure 3:
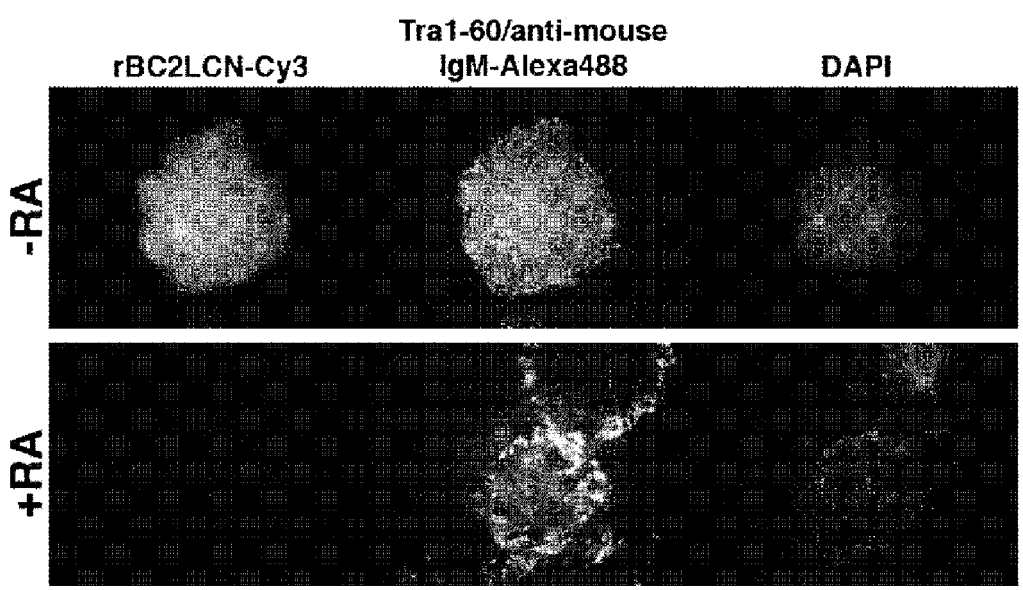
FIG. 3 is a pair of photographs of undifferentiated ES cells (KhES1 strain) and ES cells subjected to a differentiation induction treatment (the retinoic acid treatment) stained with Cy3-labeled rBC2LCN and Tral-60 (Example 2). To identify the presence of cells, nuclear staining with DAPI was performed in each case.

ES cells (KhES1 strain) were cultured by adding retinoic acid to a final concentration of $10^{-5}$ M to a culture medium thereof prepared in the same way as in Example 1 according to the method of Draper et al. (see Non Patent Literature 5) for the induction of differentiation of the ES cells. When the culture was performed for 8 days, the differentiation was confirmed to have sufficiently advanced in view of the morphology of the cells, and fluorescently labeled rBC2LCN was then reacted with the cells (FIG. 3). As a target for comparison, Tra1-60 antibody was reacted therewith, followed by further reacting anti-mouse IgM-Alexa488 as a second antibody. In the figure, the line for "+RA" shows a case of treatment with retinoic acid for differentiation toward nerve, and the line for "−RA" shows a case of untreatment. "DAPI" in the right of FIG. 3 shows the results of staining the nuclei of the same cells with DAPI.

The fluorescence of rBC2LCN was little detected in the KhES1 strain differentiated into nerve cells. In contrast, the intensity of fluorescence of Tra1-60 antibody remained to a sufficiently observable extent. These experimental results indicate that the glycoprotein antigen recognized by Tra1-60 antibody used as a known undifferentiation marker has an appreciable expression level while still maintaining a state of advanced differentiation on the cell surface whereas the sugar chain structure "Fucα1-2Galβ1-3GlcNAc/GalNAc" recognized by rBC2LCN has been expressed so as to cover the cell surface in an undifferentiated state but is almost no longer expressed when differentiation advances.

The above results have demonstrated that the sugar chain structure "Fucα1-2Galβ1-3GlcNAc/GalNAc" was an extremely excellent marker as an undifferentiation sugar chain marker for determining differentiation or undifferentiation. The rBC2LCN-immobilized substrate was found to be highly useful as an excellent kit for determining differentiation or undifferentiation, specifically recognizing stem cells, such as ES cells and iPS cells, having characteristics being undifferentiated.

Example 3

Direct Analysis of Fluorescently Labeled Culture Supernatant iPS cells (201B7 strain and 253G1 strain) used in this experiment were obtained from Riken BioResource Center. TIGMKOS#19 strain of the same cells were established in Research Center for Stem Cell Engineering, National Institute of Advanced Industrial Science and Technology (paper unpublished). Cells were cultured by the method of Tateno et al. (see Non Patent Literature 1). A culture medium cultured for about 24 hours was recovered, and only liquid components were separated by centrifugation to provide a culture supernatant.

Figure 4:
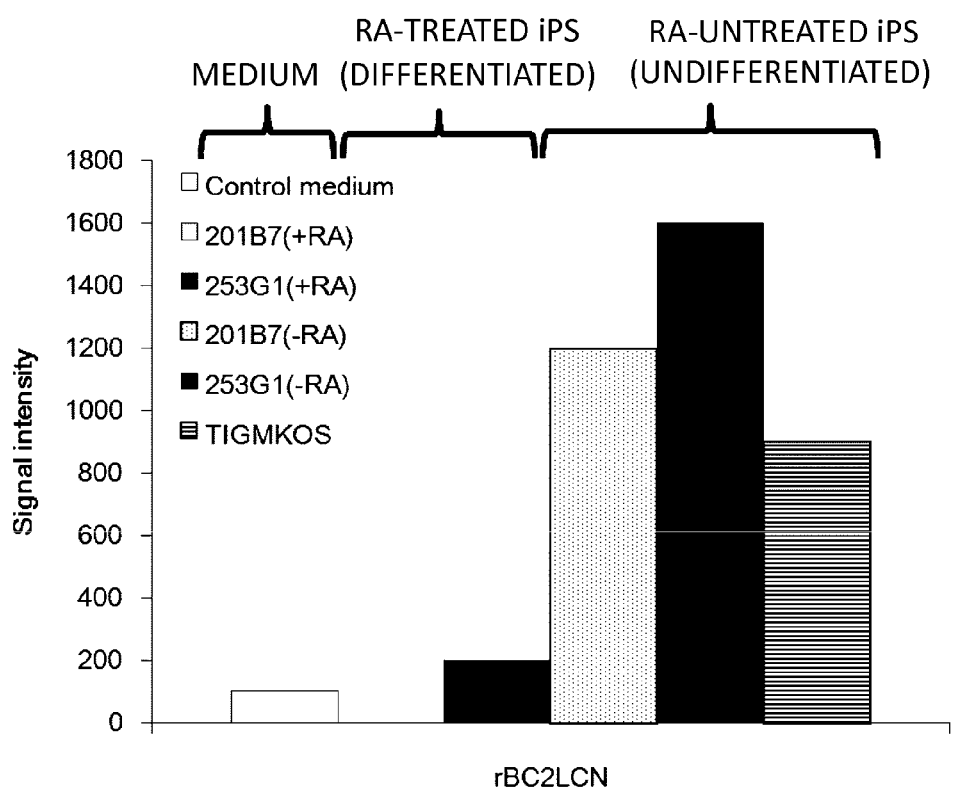
FIG. 4 is a graph showing the results of comparison between the reactivity to rBC2LCN of a culture supernatant of iPS cells (201B7 strain and 253G1 strain) subjected to a differentiation induction treatment (the retinoic acid treatment) and a culture supernatant of untreated iPS cells (201B7 strain, 253G1 strain, and TIGMKOS#19 strain) in an undifferentiated state (Example 3). Measurement was performed in the case of only the medium as a control.

Using immobilized rBC2LCN, it was examined whether the sugar chain structure "Fucα1-2Galβ1-3GlcNAc/GalNAc" was present in the culture supernatant or not. Specifically, the 201B7 and 253G1 strains of iPS cells were cultured for 8 days for differentiation induction in the same way as in Example 2. As a control, the 201B7 and 253G1 strains of the same iPS cells were also cultured for the same days in the absence of retinoic acid (RA). TIGMKOS#19 strain was also cultured for 4 days in the absence of retinoic acid (RA). The culture medium was daily replaced with a fresh culture medium, and the resultant culture supernatant to be discarded was provided for the following measurement step. The culture supernatant of each iPS cells was fluorescently labeled, reacted with rBC2LCN immobilized on a glass slide at 20° C. overnight, and washed, followed by detecting the binding using an evanescent wave excitation fluorescence scanner (FIG. 4).

As a result, rBC2LCN reacted with the culture supernatant of iPS cells (201B7, 253G1, and TIGMKOS#19 strains) remaining undifferentiated and cultured in the absence of retinoic acid, but did not have reactivity with differentiated iPS cells (201B7 and 253G1 strains) cultured in the presence of retinoic acid or a control medium. This demonstrates that the sugar chain structure "Fucα1-2Galβ1-3GlcNAc/GalNAc" effectively functions as an undifferentiation sugar chain marker for determining differentiation or undifferentiation in the culture supernatant.

Using these properties, it is possible to verify the establishment of ES cells and iPS cells using the culture supernatant without collecting cells. In culturing stem cells or in attempting to cause the cells to proliferate while having characteristics being undifferentiated, it is also possible to verify that they are not contaminated with differentiated cells. Using these properties, it is possible to simply and rapidly detect cells remaining while having characteristics being undifferentiated by simply examining the culture supernatant when various organ cells (heart muscle cells, liver cells, nerve cells, pancreatic islet cells, chondrocytic cells, bone cells, and the like) have been prepared from stem cells such as ES cells and iPS cells Proteins such as Nanog, POU5F1, DNMT3B, TERT, UTF1 (undifferentiated embryonic cell transcription factor 1), FOXD3, LIN28, and BRIX have been conventionally well-known as markers for undifferentiated cells; however, most of these proteins are located in the nuclei and the detection thereof in a culture medium is probably impossible.

Example 4

Analysis of Culture Supernatant by Lectin Overlay

To more sensitively detect an undifferentiation sugar chain marker in a culture medium, detection by a lectin-lectin sandwich method was attempted by binding a lectin for detection (lectin 2) to the undifferentiation sugar chain marker captured by rBC2LCN (lectin 1) on a glass slide. Biotinylated rAAL was used as a lectin for detection.

Figure 5:
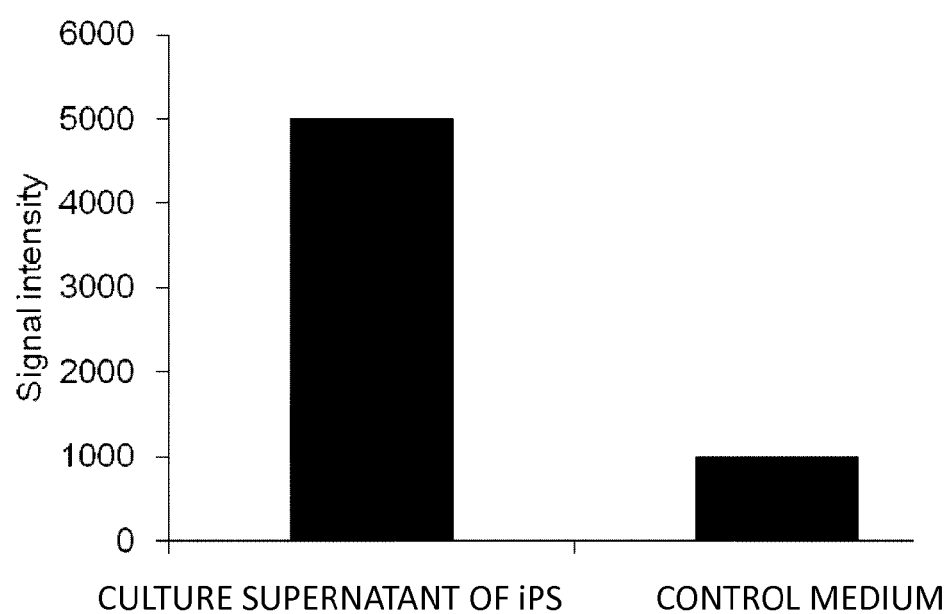
FIG. 5 is a graph showing the results of detecting an undifferentiation sugar chain marker by a lectin-lectin sandwich method (Example 4).

Specifically, the culture supernatants obtained by culturing iPS cells (TIGMKOS#19 strain) in the absence of retinoic acid (RA) and only the medium (control medium) for 4 days in Example 3 were collected and reacted with rBC2LCN immobilized on a glass slide at 20° C. overnight. After washing, bitinylated rAAL was reacted therewith at 20° C. overnight, followed by reacting streptavidin labeled with 1 μg/mL Cy3 at 20° C. for 30 minutes and then detecting the binding using an evanescent wave excitation fluorescence scanner (FIG. 5). The same treatment and measurement were also carried out for the control medium.

The results of this Example demonstrated that the undifferentiation sugar chain marker in the culture supernatant could be detected by the lectin-lectin sandwich method of the present invention using rBC2LCN immobilized on a glass slide and ALL labeled with biotin.

Example 5

Screening for Overlay Lectin

In this Example, to detect the undifferentiation sugar chain marker by a lectin-lectin sandwich method, screening was carried out for a lectin usable as a lectin for detection (overlay lectin) together with rBC2LCN as a lectin for capture. Recombinant lectins used as targets for screening are shown in "Table 1" below.

TABLE 1

| Name of Lectin | Origin | Data Base* | Accession Number |
|---|---|---|---|
| FLAG-EW29Ch | Lumbricus terrestris | PDB | 2ZQN |
| FLAG-EW29Ch-E20K | mutatnt | | — |
| rAAL | Aleuria aurantia | PDB | 1OFZ |
| rABA | Agaricus bisporus | PDB | 1Y2V |
| rACG | Agrocybe cylindracea | PDB | 1WW4 |
| rAOL | Aspergillus oryzae | ref.1 | * * |
| rBanana | Musa acuminata | PDB | 1X1V |
| rBC2LA | Burkholderia cenocepacia | PDB | 2WRA |
| rBC2LCN | Burkholderia cenocepacia | PDB | 2WQ4 |
| rC14 | Gallus gallus domesticus | NCBI | M11674 |
| rCalsepa | Calystegia sepium | PDB | 1OUW |
| rCGL2 | Coprinopsis cinerea | PDB | 1ULD |
| rCGL3 | Coprinopsis cinerea | PDB | 2R0F |
| rCNL | Clitocybe nebularis | PDB | 3NBE |
| rDiscoidin I | Dictyostelium Discodeum | PDB | 2W94 |
| rDiscoidin II | Dictyostelium Discodeum | PDB | 2VM9 |
| rEW29 | Lumbricus terrestris | PDB | 2ZQN |

TABLE 1-continued

| Name of Lectin | Origin | Data Base* | Accession Number |
|---|---|---|---|
| rF17AG | Escherichia coli | PDB | 3F6J |
| rGal1 | Homo sapiens | PDB | 1GZW |
| rGal2 | Homo sapiens | PDB | 1HLC |
| rGal3C | Homo sapiens | PDB | 1A3K |
| rGal4C | Homo sapiens | PDB | 1X50 |
| rGal4N | Homo sapiens | NCBI | NP_006140 |
| rGal7 | Homo sapiens | PDB | 1BKZ |
| rGal8C | Homo sapiens | PDB | 3OJB |
| rGal8N | Homo sapiens | PDB | 2YV8 |
| rGal9C | Homo sapiens | PDB | 3NV1 |
| rGal9N | Homo sapiens | PDB | 2YY1 |
| rGC2 | Geodia cydonium | NCBI | X70849 |
| rHeltuba | Helianthus tuberosus | PDB | 1C3K |
| rLSLN | Laetiporus sulphureus | PDB | 1W3A |
| rMalectin | Homo sapiens | NCBI | EAW98213 |
| rMOA | Marasmius oreades | PDB | 2IHO |
| rMR-Cys | Homo sapiens | NCBI | NP_032651 |
| rOrysata | Oryza sativa | NCBI | AAB53810 |
| rPAIIL | Pseudomonas aeruginosa | NCBI | NP_252051 |
| rPAIL | Pseudomonas aeruginosa | NCBI | AAT49409 |
| rPALa | Phlebodium aureum | NCBI | BAC55268 |
| rPPL | Pleurocybella porrigens | NCBI | BAG85345 |
| rPSL1a | Polyporus squamosus | NCBI | BAC87875 |
| rPTL | Pholiota squarrosa | | ref.2 * * |
| rRSIIL | Ralstonia solanacearum | NCBI | NP_520228 |
| rRSL | Ralstonia solanacearum | NCBI | NP_521407 |
| rSRC2 | mutatnt | PDB | 2DS0 |
| rSRL | Sclerotium rolfsii | PDB | 2OFC |
| rXCL | Xerocomus chrysenteron | PDB | 1XI0 |

Figure 6:
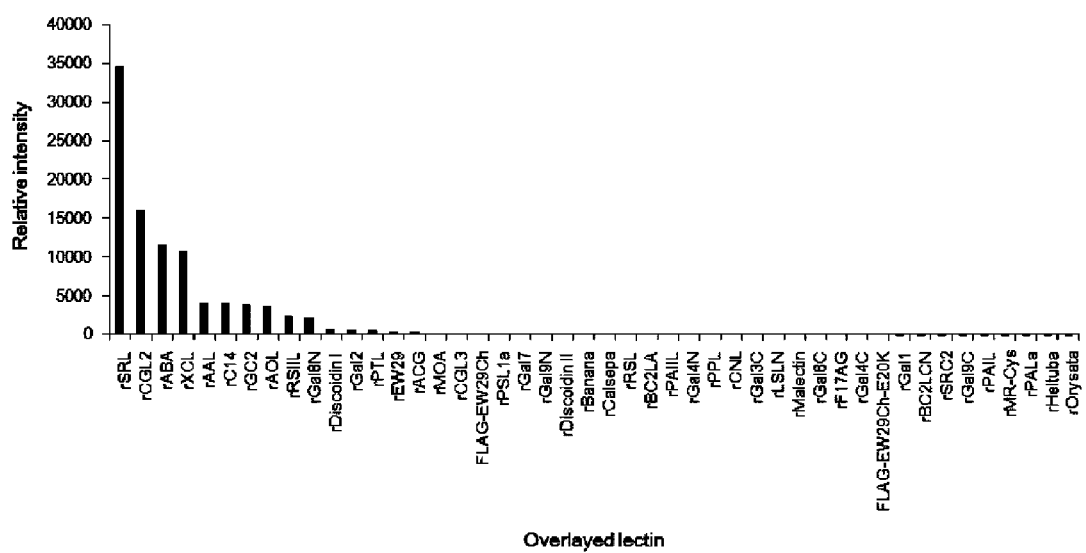
FIG. 6 is a graph showing the results of screening for detection lectins (overlay lectin) for detecting an undifferentiation sugar chain marker by a lectin-lectin sandwich method (Example 5).

*PDB: RCSB Protein Data Bank (http://www.rcsb.org/pdb/home/home.do), NCBI: National Center of Biotechnology Information (http://www.ncbi.nlm.nih.gov/pubmed)
* * Ref. 1: "Carbohydrate binding specificity of a fucose-specific lectin from *Aspergillus oryzae*: a novel probe for core fucose." J Biol Chem. 2007 May 25; 282(21): 15700-8, Ref. 2: "A Novel Core Fucose-specific Lectin from the Mushroom Pholiota squarrosa." J Biol. Chem. 2012 Oct. 5; 287(41): 339 73-82.

rBC2LCN immobilized on an epoxy-activated glass slide (#1066643, SCHOTT) and a control medium or the culture supernatant at day 3 of the culture of iPS cells (TIG/MKOS) (at a lapse of about 24 hours after medium replacement, cultured for 3 days while daily performing medium displacement) was reacted at 20° C. overnight. The resultant was then washed once with a solution (25 mM Tris-HCl pH 7.5, 140 mM NaCl (TBS), 2.7 mM KCl, 1 mM CaCl2, 1 mM MnCl2, and 1% Triton X-100). Thereafter, a Cy3-labeled recombinant lectin was added thereto, which was then incubated at 20° C. for 3 hours. The results of measuring the fluorescence intensity using GlycoStation™ Reader 1200 (GP BioSciences) are shown in FIG. 6. The vertical axis in the figure represents the value obtained by subtracting the value of fluorescence intensity obtained for the control medium from the value of fluorescence intensity obtained for the culture supernatant.

As shown in FIG. 6, particularly dominant values of fluorescence intensity were observed for the 4 recombinant lectins of SRL, CGL2, ABA, and XCL, as well as AAL used in Example 4. This demonstrated that these 4 lectins were useful as lectins for detection in detecting the undifferentiation sugar chain marker by the lectin-lectin sandwich method.

Example 6

Lectin-Lectin Sandwich Method (Recombinant Lectin)

In this Example, the undifferentiation sugar chain marker was detected by a lectin-lectin sandwich method using rSRL, rCGL2, rABA, or rXCL identified in Example 5 as lectin 2 (a lectin for detection) and using rBC2LCN as lectin 1 (a lectin for capture).

Biotinylated rBC2LCN was immobilized on a streptavidin plate (Nunc, #436020). iPS cells were cultured on the plate after washing in the presence or absence of retinoic acid (RA) for 8 days while daily performing medium replacement, and thereto was added dropwise a culture supernatant obtained by recovering the culture supernatant at day 8 of the culture (at a lapse of about 24 hours after medium replacement) for reaction at 37° C. for 1 hour. Each of the above recombinant rectins labeled with HRP was added to the plate washed again for reaction at 37° C. for 1 hour. After washing, 1-step ULTRA TMB-ELISA (Thermo, #34028) was added dropwise thereto for reaction at room temperature for 30 minutes, followed by terminating the reaction by adding 1 M sulfuric acid and then measuring absorbance at 450 nm.

Figure 7:
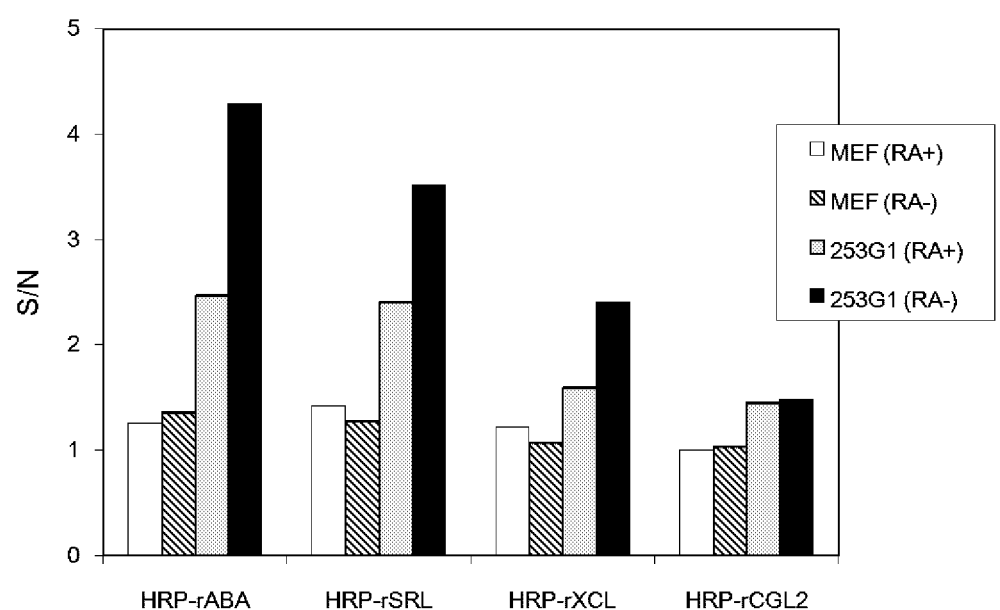
FIG. 7 is a graph showing the results of detecting an undifferentiation sugar chain marker by a lectin-lectin sandwich method (Example 6).

The results are shown in FIG. 7. In FIG. 7, as S/N was expressed the value obtained by dividing the value of absorbance obtained for the culture supernatant by the value of absorbance obtained for a control medium. When either lectin was reacted, the culture supernatant of undifferentiated iPS cells (253G1 (RA-)) exhibited a high S/N value whereas the culture supernatant of differentiated iPS cells (253G1 (RA+)) exhibited a lower S/N value. Of 4 overlay lectins, rABA exhibited the highest S/N value. In contrast, a culture supernatant of feeder cells (MEF) exhibited almost comparable reactivity to the control medium despite the addition of retinoic acid (RA).

Example 7

Preparation of Standard Curve in Lectin-Lectin Sandwich Method

In this Example, a standard curve for quantitating the number of undifferentiated cells in a culture supernatant in a system for detecting the undifferentiation sugar chain marker by the lectin-lectin sandwich method constructed in Example 6 was generated.

Figure 8:
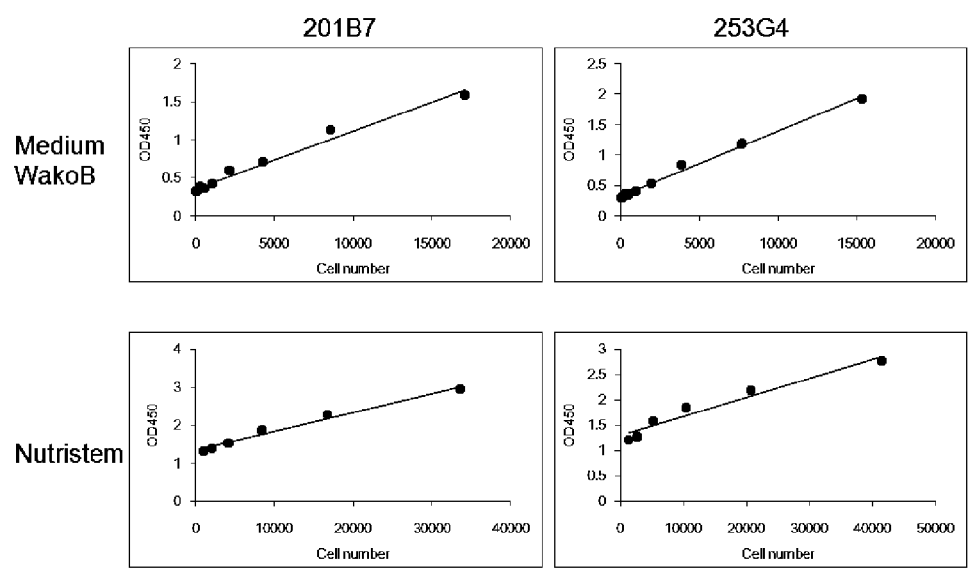
FIG. 8 is a series of graphs showing standard curves of the number of undifferentiated cells in a lectin-lectin sandwich method (Example 7).
Figure 9:
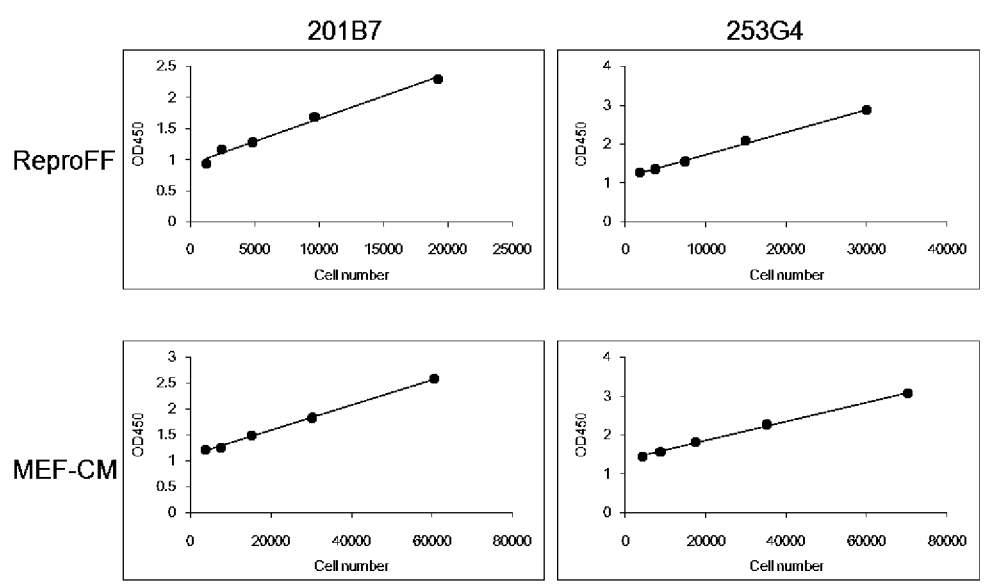
FIG. 9 is a series of graphs showing standard curves of the number of undifferentiated cells in a lectin-lectin sandwich method (Example 7).
Figure 10:
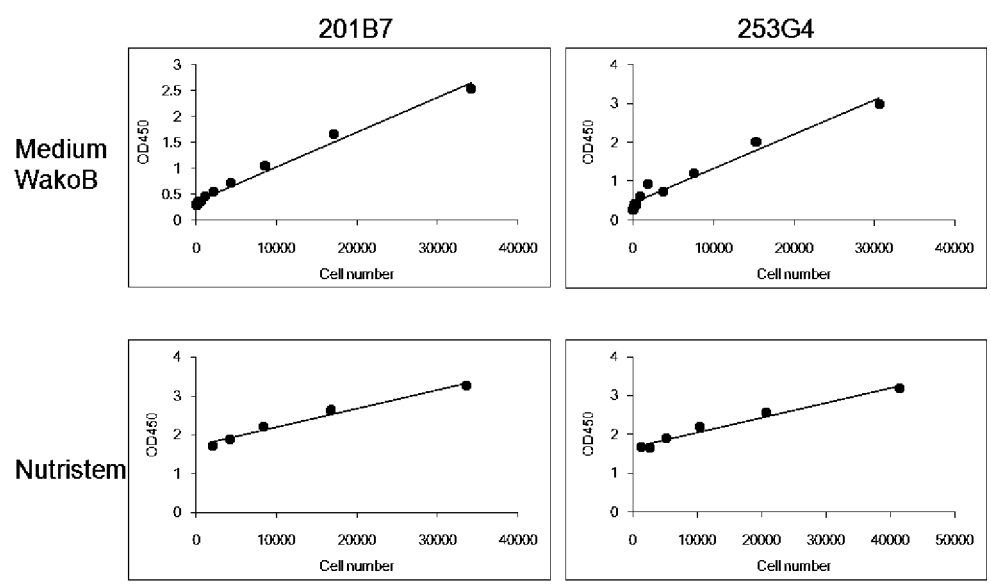
FIG. 10 is a series of graphs showing standard curves of the number of undifferentiated cells in a lectin-lectin sandwich method (Example 7).
Figure 11:
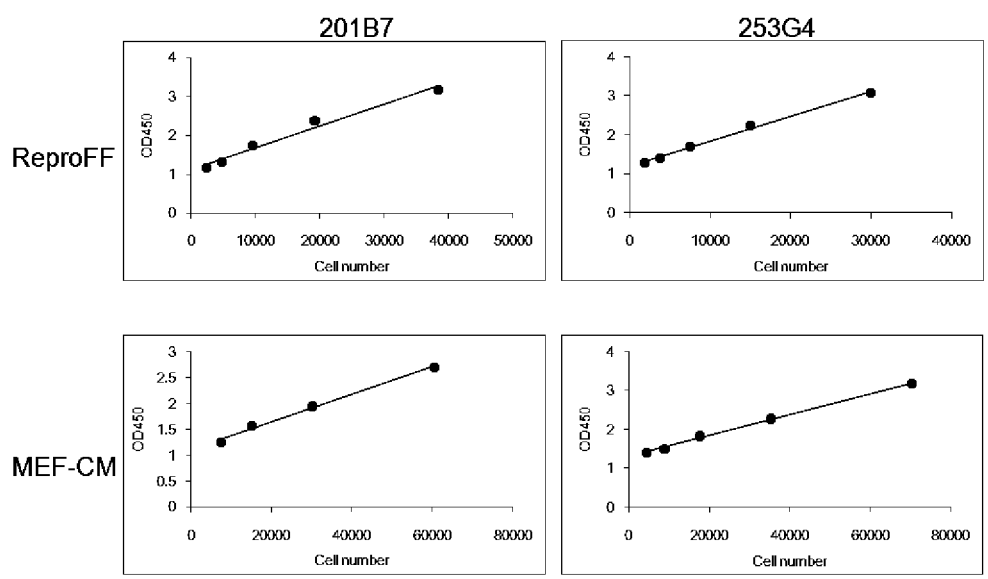
FIG. 11 is a series of graphs showing standard curves of the number of undifferentiated cells in a lectin-lectin sandwich method (Example 7).

After culturing iPS cells (201B7 or 253G4) for 24 hours, the medium (Medium WakoB, Nutristem, ReproFF, or MEF-CM) was recovered, and the number of iPS cells in the medium was counted. The culture supernatant of iPS cells was serially diluted and analyzed in the same way as in Example 6 to provide a regression line showing the relationship between the resultant value of absorbance and the number of cells as a standard curve. The standard curves obtained using rABA as a lectin for detection are shown in FIGS. 8 and 9, and the standard curves obtained using rSRL are shown in FIGS. 10 and 11. Each of the standard curves shown in FIGS. 8 to 11 exhibited a correlation coefficient of as high as 0.961 or more.

The results of this Example indicates that the measurement of the undifferentiation sugar chain marker in the culture supernatant using a combination of particular lectins can quantitatively detect undifferentiated cells to determine whether the number of the undifferentiated cells is 0 or not.

Example 8

Identification of Undifferentiation Sugar Chain Marker

In this Example, the identification of the undifferentiation sugar chain marker was performed.

1 mL each of the culture supernatant (KhES1 sup) of ES cells obtained by culture for 3 days while daily performing medium replacement, the culture supernatant (253G1 sup) of iPS cells obtained by culture for 3 days (at a lapse of about 24 hours after medium replacement), and the respective control media were each taken, mixed with rBC2LCN-immobilized beads, and reacted at room temperature for 3 hours. After reaction, the beads were heated at 95° C. for 5 minutes in 100 µL of 0.2% SDS to elute a binding fraction. 10 µL of the binding fraction was subjected to acrylamide gel electrophoresis, stained with silver, and blotted with HRP-rABA or HRP-rSRL.

Figure 12:
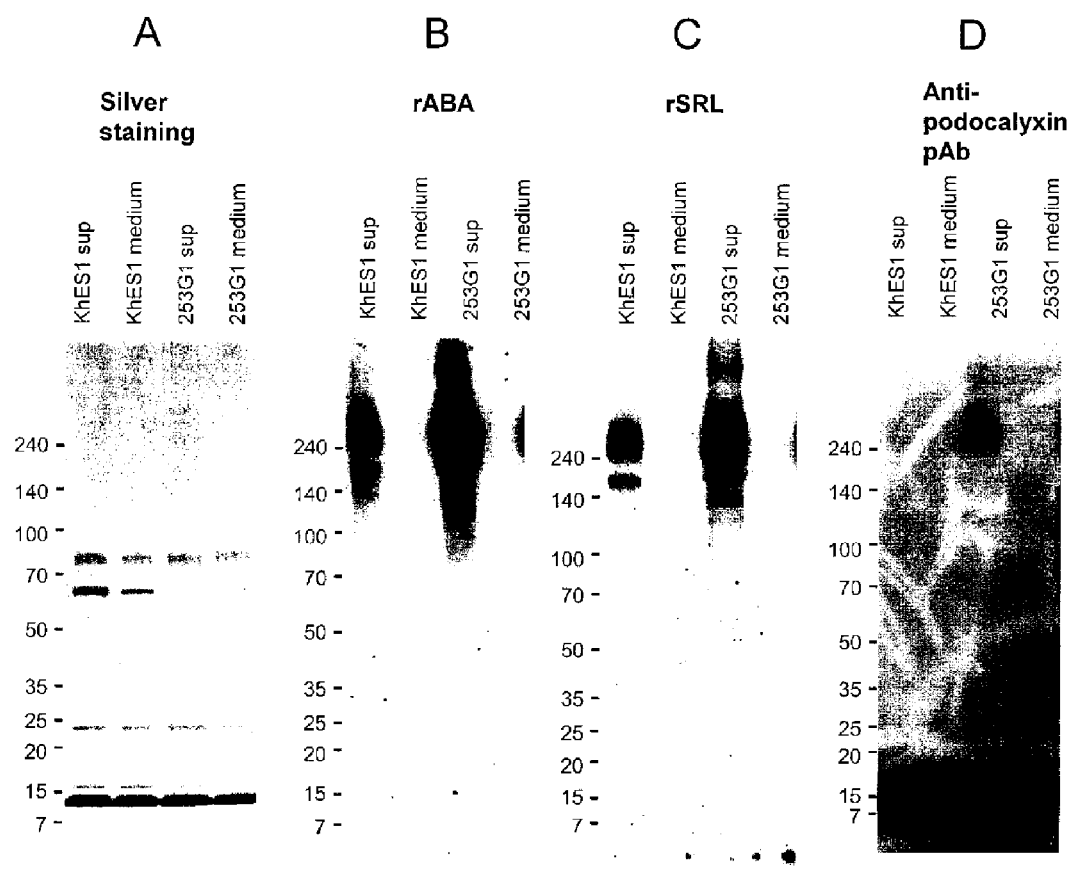
FIG. 12 is a series of photographs showing the results of identifying an undifferentiation sugar chain marker (Example 8).

The results are shown in A to C of FIG. 12. In the blotting with HRP-rABA and HRP-rSRL, molecules having molecular weights of 240 kDa or more gave signals (see B and C).

In addition, the results of blotting with an anti-podocalyxin antibody are shown in FIG. 12-D. Signals were observed for molecules having molecular weights of 240 kDa or more, and these molecules were each demonstrated to be podocalyxin protein or a portion of podocalyxin protein.

From these results, podocalyxin was identified as an undifferentiated sugar marker. Podocalyxin is a type 1 transmembrane glycoprotein, identified from epithelial glomerular cells known as podocytes, and known to be associated with the development of various cancers as well as to play important roles in keeping the function/morphology of the glomerulus (see Non Patent Literature 8).

From the results of this Example and the results of an experiment in which the alkaline digestion of podocalyxin was performed, podocalyxin was expected to contain "Fucα1-2Galβ1-3GalNAc (H type 3 sugar chain)" in the modifying sugar chain. However, it is not clear whether the H type 1 sugar chain is present in podocalyxin or not.

The identification of podocalyxin having the H type 3 sugar chain in this Example indicates the possibility that the anti-podocalyxin antibody specifically recognizing the glycosylation site with the H type 3 sugar chain of podocalyxin can be used as a probe for detecting undifferentiated cells.

Example 9

Analysis of Binding Property of rBC2LCN

In this Example, the sugar chain structure recognized by rBC2LCN was analyzed.

According to the method of Tateno et al. (see Non Patent Literature 7), rBC2LCN was immobilized on NHS-activated Sepharose 4FF (GE) and packed into a minicolumn (inner diameter, 2 mm; length, 10 mm, bed volume, 31.4 µL), which was then connected to high-performance liquid chromatography. A pyridylaminated sugar chain isolated from human iPS cells (201B7) was injected into the column, and fluorescence was detected at an excitation of 285 nm and a fluorescence of 350 nm. As a result of analysis, rBC2LCN was found to bind to a type O sugar chain containing H type 3 isolated from iPS cells with an affinity of Ka=$2.5 \times 10^4$ M$^{-1}$ (see FIG. 13).

Figure 13:
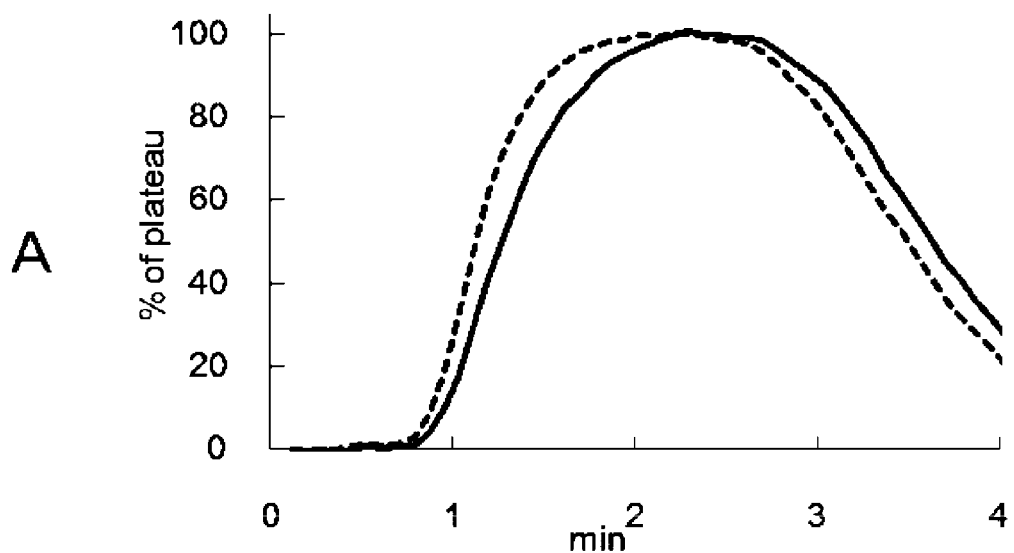
FIG. 13 is a graph showing the results of analyzing the sugar chain structure recognized by rBC2LCN (Example 9).
Figure 13:

In FIG. 13-A, the dotted line denotes an elusion profile of Manα1-6(Manα1-3) Manβ1-4GlcNAcβ1-4GlcNAc-PA as a control sugar chain subjected to PA. The solid line denotes an elution profile of Fucα1-2Galβ1-3(Galβ1-3GlcNAcβ1-6)GalNAc-PA as a sugar chain subjected to PA isolated from iPS cells. FIG. 13-B is a schematic representation of Fucα1-2Galβ1-3(Galβ1-3GlcNAcβ1-6)GalNAc-PA (type O sugar chain containing H type 3). The circle represents galactose; the open box, N-acetylgalactosamine; the closed box, N-acetylglucosamine; and the triangle, fucose. The thick lines between galactose and N-acetylglucosamine and between galactose and N-acetylgalactosamine represent β linkages, and the thin line between galactose and fucose represents an a linkage.

Reference Example 10

Comparative Experiment Using Natural Lectin

In this reference example, the problem of a case where a lectin having a sugar chain was used in a lectin-lectin sandwich method was verified.

PNGaseF was added dropwise to a high-density natural lectin array (see Non Patent Literature 1) in which 96 lectins were immobilized on a glass slide, followed by reaction at 37° C. overnight. After reaction, the resultant was washed once, and a Cy3-labeled recombinant lectin (rOrysata) was added dropwise thereto, followed by reaction at 20° C. overnight. After reaction, the resultant was washed twice, and the fluorescence intensity was measured using GlycoStation™ Reader 1200 (GP BioSciences). For comparison, the same operation was performed using a high-density natural lectin array that had not been treated with PNGase.

As a result, in the lectin array not treated with PNGaseF, signals were detected for SSA, SNA, RCA120, and MCA, and rOrysata was bound to these 4 lectins. In contrast, signals from SSA, SNA, RCA120, and MCA disappeared in the lectin array treated with PNGaseF. This indicates that when a lectin having a sugar chain is used in the lectin-lectin sandwich method, an undesired complex is formed by the binding of lectins to each other via the sugar chain of the lectins themselves without being via a substance to be detected. In other words, the use of a natural lectin in the lectin-lectin sandwich method was demonstrated to increase the possibility of causing false positivity in the sugar chain detection.

Example 11

Lectin Sandwich Method (Sugar Chain-Removed Natural Lectin)

In this Reference Example, a glycoprotein was detected by the lectin-lectin sandwich method by using a modified lectin array obtained by treating a natural lectin array with a glycolytic enzyme.

PNGaseF was added dropwise to the natural lectin array used in Reference Example 10, which was then incubated at 37° C. overnight. After incubation, the resultant was washed twice, and thyroglobulin (10 μg/mL) was added dropwise thereto, which was then reacted at 37° C. overnight. After reaction, the resultant was washed twice, and a Cy3-labeled recombinant lectin (rOrysata) was added dropwise thereto, which was then reacted at 20° C. for 3 hours. After reaction, the resultant was washed twice, and the fluorescence intensity was measured using GlycoStation™ Reader 1200 (GP BioSciences). For comparison, the same operation was performed without adding dropwise thyroglobulin to calculate the ratio of the fluorescence intensity value obtained using the array to which thyroglobulin was added dropwise (signal) to the fluorescence intensity value obtained using the array to which it was not added dropwise (noise) (S/N ratio). From the sugar chain structure of thyroglobulin, it was expected that SSA, SNA, RCA120, MCA, and rOrysata each have a binding property to thyroglobulin.

The results are shown in "Table 2".

TABLE 2

| Lectin for | S/N Ratio | |
|---|---|---|
| Capture | PNGase Non-Treatment | PNGase Treatment |
| SSA | 1.9 | 8.0 |
| SNA | 1.5 | 6.0 |
| RCA120 | 1.7 | 3.6 |
| MCA | 3.1 | 6.5 |

The S/N ratio was about 1.9 for SSA (natural lectin) in the lectin array that had not been treated with PNGaseF. In contrast, the S/N ratio was significantly improved to about 8.0 for SSA (sugar chain-removed natural lectin) in the lectin array treated with PNGaseF. Similarly, the S/N ratio for the detection of thyroglobulin was significantly improved in the PNGaseF-treated lectin array compared to the PNGaseF-untreated lectin array also for SSA, SNA, RCA120, and MCA.

From these results and the results of Example 10, it is thought that in the PNGaseF-untreated array, rOrysata (lectin for detection) directly binds to SSA, SNA, RCA120, or MCA (lectin for capture) without being via thyroglobulin (substance to be detected), which produces noise. In contrast, in the PNGaseF-treated array, the removal of the sugar chain of the lectin for capture prevented the direct binding between the lectin for detection and the lectin for capture, enabling the sensitive detection of a signal generated from a complex of the lectin for capture, the substance to be detected, and the lectin for detection.

The results of this Example demonstrated that when the lectin-lectin sandwich method is performed, the elimination of the influence of the sugar chain of a lectin could prevent the binding of another lectin to the sugar chain of the lectin used to keep measurement background at a low level and sensitively measure the substance to be detected.

REFERENCE SIGN LIST

1: Complex 1 (a complex of lectin $L_1$ and substance to be detected T), 2: Complex 2 (a complex of lectin $L_1$, substance to be detected T, and lectin $L_2$), $L_1$: lectin 1, $L_2$: lectin 2, $G_1$, $G_2$: Sugar chain structures, S: Solid phase surface, T: Substance to be detected.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "PSK-9020US_Sequence-Listing.txt", created Apr. 21, 2014, file size of 8,192 bytes, is hereby incorporated by reference.

The invention claimed is:

1. A method of determining whether stem cells in a culture are completely differentiated or not, comprising:
   (1) obtaining a culture supernatant from the culture of the stem cells; and
   (2) measuring the presence or absence of an undifferentiation sugar chain marker represented by:
   (i) formula 1:

(Formula 1)

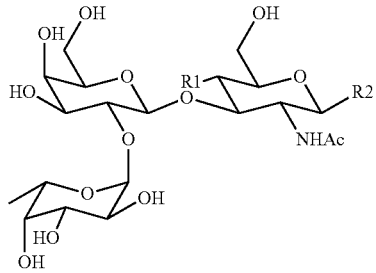

wherein R1 represents an OH group or any sugar chain and R2 represents an OH group or any sugar chain, protein, lipid, or another molecule, or
   (ii) formula 2:

(Formula 2)

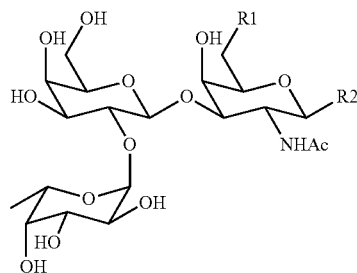

wherein R1 represents an OH group or any sugar chain and R2 represents an OH group or any sugar chain, protein, lipid, or another molecule, in the culture supernatant, in comparison to a culture supernatant from a completely differentiated stem cell negative control, wherein the presence or absence of the undifferentiation sugar chain marker is measured using a recombinant recognition protein comprising the amino acid sequence consisting of SEQ ID NO: 1 or the amino acid sequence consisting of SEQ ID NO: 1 in which one amino acid is deleted, substituted, inserted, or added, and specifically recognizing the sugar chain structure represented by the formula 1 or 2.

2. The method according to claim 1, wherein the culture supernatant is a culture supernatant of which the stem cells have been subjected to a differentiation induction treatment.

3. The method according to claim 1, comprising measuring the presence or absence of the undifferentiation sugar chain marker represented by the formula 1 and/or 2 derived from podocalyxin.

4. The method according to claim 1, comprising detecting the undifferentiation sugar chain marker by a lectin-lectin sandwich method using the recombinant recognition protein.

5. A method for obtaining completely differentiated stem cells in a culture, the method comprising:
   (1) subjecting the culture of stem cells to a differentiation induction treatment;
   (2) obtaining a culture supernatant from the culture of the stem cells;
   (3) detecting to confirm the absence of an undifferentiation sugar chain marker represented by:

(i) formula 1:

(Formula 1)

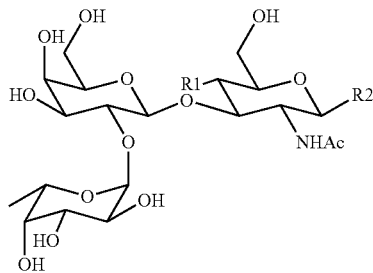

wherein R1 represents an OH group or any sugar chain and R2 represents an OH group or any sugar chain, protein, lipid, or another molecule, or (ii) formula 2:

(Formula 2)

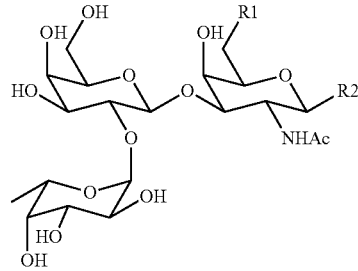

wherein R1 represents an OH group or any sugar chain and R2 represents an OH group or any sugar chain, protein, lipid, or another molecule,
in the culture supernatant, in comparison to a culture supernatant of a completely differentiated stem cell negative control; and
(4) collecting the differentiated cells from the culture following confirmation of the absence of the undifferentiated sugar chain marker from the culture supernatant,
wherein the confirmation of the absence of the undifferentiation sugar chain marker indicates complete differentiation of all cells in the culture; and
wherein the confirmation of the absence of the undifferentiation sugar chain marker is made using a recombinant recognition protein comprising the amino acid sequence consisting of SEQ ID NO: 1 or the amino acid sequence consisting of SEQ ID NO: 1 in which one amino acid is deleted, substituted, inserted, or added, and specifically recognizing the sugar chain structure represented by the formula 1 or 2.

6. The method according to claim 1, wherein the recombinant recognition protein comprises the amino acid sequence consisting of SEQ ID NO: 1, and specifically recognizes the sugar chain structure represented by the formula 1 or 2.

7. The method according to claim 1, wherein the recombinant recognition protein comprises the amino acid sequence consisting of SEQ ID NO: 1 in which one amino acid is deleted, substituted, inserted, or added, and specifically recognizes the sugar chain structure represented by the formula 1 or 2.

8. The method according to claim 5, wherein the recombinant recognition protein comprises the amino acid sequence consisting of SEQ ID NO: 1, and specifically recognizes the sugar chain structure represented by the formula 1 or 2.

9. The method according to claim 5, wherein the recombinant recognition protein comprises the amino acid sequence consisting of SEQ ID NO: 1 in which one amino acid is deleted, substituted, inserted, or added, and specifically recognizes the sugar chain structure represented by the formula 1 or 2.

10. A method for determining a degree of differentiation of stem cells in a culture, comprising:
(1) obtaining a culture supernatant from the culture of the stem cells; and
(2) measuring an amount of an undifferentiation sugar chain marker represented by:
(i) formula 1:

(Formula 1)

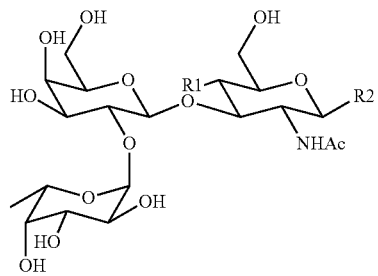

wherein R1 represents an OH group or any sugar chain and R2 represents an OH group or any sugar chain, protein, lipid, or another molecule, or (ii) formula 2:

(Formula 2)

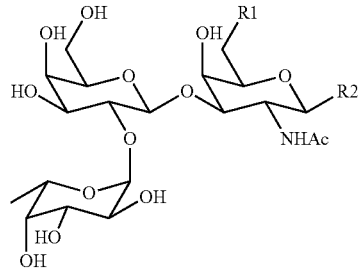

wherein R1 represents an OH group or any sugar chain and R2 represents an OH group or any sugar chain, protein, lipid, or another molecule, in the culture supernatant,
wherein the amount of the undifferentiation sugar chain marker is measured using a recombinant recognition protein comprising the amino acid sequence consisting of SEQ ID NO: 1 or the amino acid sequence consisting of SEQ ID NO: 1 in which one amino acid is deleted, substituted, inserted, or added, and specifically recognizing the sugar chain structure represented by the formula 1 or 2, and
wherein the measured amount is correlated to the degree of differentiation based on a standard curve.

11. The method according to claim 10, wherein the culture supernatant is a culture supernatant of which the stem cells have been subjected to a differentiation induction treatment.

12. The method according to claim 10, comprising measuring the amount of the undifferentiation sugar chain marker represented by the formula 1 and/or 2 derived from podocalyxin.

13. The method according to claim 10, comprising detecting the undifferentiation sugar chain marker by a lectin-lectin sandwich method using the recombinant recognition protein.

14. The method according to claim 10, wherein the recombinant recognition protein comprises the amino acid sequence consisting of SEQ ID NO: 1, and specifically recognizes the sugar chain structure represented by the formula 1 or 2.

15. The method according to claim 10, wherein the recombinant recognition protein comprises the amino acid sequence consisting of SEQ ID NO: 1 in which one amino acid is deleted, substituted, inserted, or added, and specifically recognizes the sugar chain structure represented by the formula 1 or 2.

* * * * *

SEQUENCE LISTING

<160> NUMBER OF SEQ ID NOS: 5

<210> SEQ ID NO 1
<211> LENGTH: 156
<212> TYPE: PRT
<213> ORGANISM: Burkholderia cenocepacia

<400> SEQUENCE: 1

```
Met Pro Leu Leu Ser Ala Ser Ile Val Ser Ala Pro Val Val Thr Ser
1               5                   10                  15

Glu Thr Tyr Val Asp Ile Pro Gly Leu Tyr Leu Asp Val Ala Lys Ala
            20                  25                  30

Gly Ile Arg Asp Gly Lys Leu Gln Val Ile Leu Asn Val Pro Thr Pro
        35                  40                  45

Tyr Ala Thr Gly Asn Asn Phe Pro Gly Ile Tyr Phe Ala Ile Ala Thr
    50                  55                  60

Asn Gln Gly Val Val Ala Asp Gly Cys Phe Thr Tyr Ser Ser Lys Val
65                  70                  75                  80

Pro Glu Ser Thr Gly Arg Met Pro Phe Thr Leu Val Ala Thr Ile Asp
                85                  90                  95

Val Gly Ser Gly Val Thr Phe Val Lys Gly Gln Trp Lys Ser Val Arg
            100                 105                 110

Gly Ser Ala Met His Ile Asp Ser Tyr Ala Ser Leu Ser Ala Ile Trp
        115                 120                 125

Gly Thr Ala Ala Pro Ser Ser Gln Gly Ser Gly Asn Gln Gly Ala Glu
    130                 135                 140

Thr Gly Gly Thr Gly Ala Gly Asn Ile Gly Gly Gly
145                 150                 155
```

<210> SEQ ID NO 2
<211> LENGTH: 143
<212> TYPE: PRT
<213> ORGANISM: Agaricus bisporus

<400> SEQUENCE: 2

```
Met Thr Tyr Thr Ile Ser Ile Arg Val Tyr Gln Thr Thr Pro Lys Gly
1               5                   10                  15

Phe Phe Arg Pro Val Glu Arg Thr Asn Trp Lys Tyr Ala Asn Gly Gly
            20                  25                  30

Thr Trp Asp Glu Val Arg Gly Glu Tyr Val Leu Thr Met Gly Gly Ser
        35                  40                  45

Gly Thr Ser Gly Ser Leu Arg Phe Val Ser Ser Asp Thr Asp Glu Ser
    50                  55                  60

Phe Val Ala Thr Phe Gly Val His Asn Tyr Lys Arg Trp Cys Asp Ile
65                  70                  75                  80

Val Thr Asn Leu Thr Asn Glu Gln Thr Ala Leu Val Ile Asn Gln Glu
                85                  90                  95

Tyr Tyr Gly Val Pro Ile Arg Asp Gln Ala Arg Glu Asn Gln Leu Thr
            100                 105                 110

Ser Tyr Asn Val Ala Asn Ala Lys Gly Arg Arg Phe Ala Ile Glu Tyr
        115                 120                 125

Thr Val Thr Glu Gly Asp Asn Leu Lys Ala Asn Leu Ile Ile Gly
    130                 135                 140
```

<210> SEQ ID NO 3
<211> LENGTH: 146
<212> TYPE: PRT

<213> ORGANISM: Xerocomus chrysenteron

<400> SEQUENCE: 3

Met Gly His Met Ser Tyr Ser Ile Thr Leu Arg Val Tyr Gln Thr Asn
1               5                   10                  15

Arg Asp Arg Gly Tyr Phe Ser Ile Val Glu Lys Thr Val Trp His Phe
            20                  25                  30

Ala Asn Gly Gly Thr Trp Ser Glu Ala Asn Gly Ala His Thr Leu Thr
        35                  40                  45

Gln Gly Gly Ser Gly Thr Ser Gly Val Leu Arg Phe Leu Ser Thr Lys
    50                  55                  60

Gly Glu Arg Ile Thr Val Ala Val Gly Val His Asn Tyr Lys Arg Trp
65                  70                  75                  80

Cys Asp Val Val Thr Gly Leu Lys Pro Asp Glu Thr Ala Leu Val Ile
                85                  90                  95

Asn Pro Gln Tyr Tyr Asn Asn Gly Gly Arg Asp Tyr Val Arg Glu Lys
            100                 105                 110

Gln Leu Ala Glu Tyr Ser Val Thr Ser Ala Ile Gly Thr Lys Val Glu
        115                 120                 125

Val Val Tyr Thr Val Ala Glu Gly Asn Asn Leu Glu Ala Asn Val Ile
    130                 135                 140

Phe Ser
145

<210> SEQ ID NO 4
<211> LENGTH: 142
<212> TYPE: PRT
<213> ORGANISM: Sclerotium rolfsii

<400> SEQUENCE: 4

Met Thr Tyr Lys Ile Thr Val Arg Val Tyr Gln Thr Asn Pro Asn Ala
1               5                   10                  15

Phe Phe His Pro Val Glu Lys Thr Val Trp Lys Tyr Ala Asn Gly Gly
            20                  25                  30

Thr Trp Thr Ile Thr Asp Asp Gln His Val Leu Thr Met Gly Gly Ser
        35                  40                  45

Gly Thr Ser Gly Thr Leu Arg Phe His Ala Asp Asn Gly Glu Ser Phe
    50                  55                  60

Thr Ala Thr Phe Gly Val His Asn Tyr Lys Arg Trp Cys Asp Ile Val
65                  70                  75                  80

Thr Asn Leu Ala Ala Asp Glu Thr Gly Met Val Ile Asn Gln Gln Tyr
                85                  90                  95

Tyr Ser Gln Lys Asn Arg Glu Glu Ala Arg Glu Arg Gln Leu Ser Asn
            100                 105                 110

Tyr Glu Val Lys Asn Ala Lys Gly Arg Asn Phe Glu Ile Val Tyr Thr
        115                 120                 125

Glu Ala Glu Gly Asn Asp Leu His Ala Asn Leu Ile Ile Gly
    130                 135                 140

<210> SEQ ID NO 5
<211> LENGTH: 150
<212> TYPE: PRT
<213> ORGANISM: Coprinopsis cinerea

<400> SEQUENCE: 5

```
Met Leu Tyr His Leu Phe Val Asn Asn Gln Val Lys Leu Gln Asn Asp
1               5                   10                  15

Phe Lys Pro Glu Ser Val Ala Ala Ile Arg Ser Ser Ala Phe Asn Ser
                20                  25                  30

Lys Gly Gly Thr Thr Val Phe Asn Phe Leu Ser Ala Gly Glu Asn Ile
        35                  40                  45

Leu Leu His Ile Ser Ile Arg Pro Gly Glu Asn Val Ile Val Phe Asn
        50                  55                  60

Ser Arg Leu Lys Asn Gly Ala Trp Gly Pro Glu Glu Arg Ile Pro Tyr
65                  70                  75                  80

Ala Glu Lys Phe Arg Pro Pro Asn Pro Ser Ile Thr Val Ile Asp His
                85                  90                  95

Gly Asp Arg Phe Gln Ile Arg Phe Asp Tyr Gly Thr Ser Ile Tyr Tyr
                100                 105                 110

Asn Lys Arg Ile Lys Glu Asn Ala Ala Ala Ile Ala Tyr Asn Ala Glu
            115                 120                 125

Asn Ser Leu Phe Ser Ser Pro Val Thr Val Asp Val His Gly Leu Leu
            130                 135                 140

Pro Pro Leu Pro Pro Ala
145             150
```